US010239922B2

(12) United States Patent
Liu et al.

(10) Patent No.: US 10,239,922 B2
(45) Date of Patent: *Mar. 26, 2019

(54) FUSION PROTEINS OF SUPERFOLDER GREEN FLUORESCENT PROTEIN AND USE THEREOF

(71) Applicant: Suzhou Kunpeng Biotech Co., Ltd., Kunshan, Suzhou (CN)

(72) Inventors: Wenshe Liu, College Station, TX (US); Wei Wan, College Station, TX (US)

(73) Assignee: Suzhou Kunpeng Biotech Co., Ltd., Kunshan, Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/638,145

(22) Filed: Jun. 29, 2017

(65) Prior Publication Data

US 2018/0016310 A1    Jan. 18, 2018

Related U.S. Application Data

(63) Continuation of application No. 14/387,456, filed as application No. PCT/US2013/033702 on Mar. 25, 2013, now Pat. No. 9,714,274.

(60) Provisional application No. 61/615,178, filed on Mar. 23, 2012.

(51) Int. Cl.
*C07K 14/61* (2006.01)
*C07K 14/62* (2006.01)
*C07K 14/435* (2006.01)
*C07K 14/585* (2006.01)
*C07K 14/605* (2006.01)
*C07K 14/635* (2006.01)

(52) U.S. Cl.
CPC ...... *C07K 14/43595* (2013.01); *C07K 14/585* (2013.01); *C07K 14/605* (2013.01); *C07K 14/62* (2013.01); *C07K 14/635* (2013.01); *C07K 2319/00* (2013.01); *C07K 2319/21* (2013.01); *C07K 2319/50* (2013.01)

(58) Field of Classification Search
CPC ............ C07K 14/43595; C07K 14/585; C07K 14/605; C07K 14/62; C07K 14/61
See application file for complete search history.

(56) References Cited

U.S. PATENT DOCUMENTS

| 6,803,188 | B1 | 10/2004 | Tsien et al. |
| 7,390,639 | B2 | 6/2008 | Su et al. |
| 7,390,640 | B2 * | 6/2008 | Waldo ............... C07K 14/43595 435/189 |
| 2011/0112040 | A1 | 5/2011 | Liu et al. |

OTHER PUBLICATIONS

Fahnert et al., Adv Biochem Engin/Biotecnol, 89, 93-142, 2004.*
Cava, F. et al. "Expression and use of superfolder green fluorescent protein at high temperatures in vivo: a tool to study extreme thermophile biology", Environmental Microbiology, Jan. 7, 2008, vol. 10, No. 3, pp. 605-613.
GenBank accession No. HQ873313.1, Feb. 9, 2011.
Solovyov, K. V. et al. "Expression in *E. coli* and purification of the fibrillogenic fusion proteins TTR-sfGFP and β2M-sfGFP", Preparative Biochemistry & Biotechnology, Oct. 3, 2011, vol. 41, No. 4, pp. 337-349.
Wu, Xudong et al., "A novel method for high-level production of TEV protease by superfolder GFP tag", Journal of Biomedicine and Biotechnology, 2010, vol. 2009, 591923, pp. 1-8.

* cited by examiner

*Primary Examiner* — Maryam Monshipouri
(74) *Attorney, Agent, or Firm* — Cooley LLP; Heidi A. Erlacher; Chun L. Yu

(57) ABSTRACT

The present disclosure pertains to methods of producing recombinant peptides that contain between 10 and 200 amino acid residues using novel carrier proteins derived from superfolder green fluorescent protein and its mutants.

10 Claims, 10 Drawing Sheets

Specification includes a Sequence Listing.

SEQUENCE LISTING

<160> NUMBER OF SEQ ID NOS: 72

<210> SEQ ID NO 1
<211> LENGTH: 237
<212> TYPE: PRT
<213> ORGANISM: Artificial Sequence
<220> FEATURE:
<223> OTHER INFORMATION: Superfolder green fluorescent protein sequence

<400> SEQUENCE: 1

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Arg Gly Glu Gly
            20                  25                  30

Glu Gly Asp Ala Thr Asn Gly Lys Leu Thr Leu Lys Phe Ile Cys Thr
        35                  40                  45

Thr Gly Lys Leu Pro Val Pro Trp Pro Thr Leu Val Thr Thr Leu Thr
    50                  55                  60

Tyr Gly Val Gln Cys Phe Ser Arg Tyr Pro Asp His Met Lys Arg His
65                  70                  75                  80

Asp Phe Phe Lys Ser Ala Met Pro Glu Gly Tyr Val Gln Glu Arg Thr
                85                  90                  95

Ile Ser Phe Lys Asp Asp Gly Thr Tyr Lys Thr Arg Ala Glu Val Lys
            100                 105                 110

Phe Glu Gly Asp Thr Leu Val Asn Arg Ile Glu Leu Lys Gly Ile Asp
        115                 120                 125

Phe Lys Glu Asp Gly Asn Ile Leu Gly His Lys Leu Glu Tyr Asn Phe
    130                 135                 140

Asn Ser His Asn Val Tyr Ile Thr Ala Asp Lys Gln Lys Asn Gly Ile
145                 150                 155                 160

Lys Ala Asn Phe Lys Ile Arg His Asn Val Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Ser Val Leu Ser Lys
        195                 200                 205

Asp Pro Asn Glu Lys Arg Asp His Met Val Leu Leu Glu Phe Val Thr
    210                 215                 220

Ala Ala Gly Ile Thr His Gly Met Asp Glu Leu Tyr Lys
225                 230                 235

<210> SEQ ID NO 2
<211> LENGTH: 712
<212> TYPE: DNA
<213> ORGANISM: Artificial Sequence
<220> FEATURE:
<223> OTHER INFORMATION: Superfolder green fluorescent protein
      nucleotide sequence

<400> SEQUENCE: 2

```
agcaaaggtg aagaactgtt taccggcgtt gtgccgattc tggtggaact ggatggtgat    60
gtgaatggcc ataaatttag cgttcgtggc gaaggcgaag gtgatgcgac caacggtaaa   120
ctgaccctga aatttatttg caccaccggt aaactgccgg ttccgtggcc gaccctggtg   180
accaccctga cctatggcgt tcagtgcttt agccgctatc cggatcatat gaaacgccat   240
gatttcttta aaagcgcgat gccggaaggc tatgtgcagg aacgtaccat tagcttcaaa   300
gatgatggca cctataaaac ccgtgcggaa gttaaatttg aaggcgatac cctggtgaac   360
cgcattgaac tgaaaggtat tgattttaaa gaagatggca acattctggg tcataaactg   420
gaatataatt tcaacagcca taatgtgtat attaccgccg ataaacagaa aaatggcatc   480
aaagcgaact ttaaaatccg tcacaacgtg gaagatggta gcgtgcagct ggcggatcat   540
tatcagcaga ataccccgat tggtgatggc ccggtgctgc tgccggataa tcattatctg   600
agcacccaga gcgttctgag caaagatccg aatgaaaaac gtgatcatat ggtgctgctg   660
gaatttgtta ccgccgcggg cattacccac ggtatggatg aactgtataa ag           712
```

<210> SEQ ID NO 3
<211> LENGTH: 7
<212> TYPE: PRT
<213> ORGANISM: Artificial Sequence
<220> FEATURE:
<223> OTHER INFORMATION: amino acid sequence of a TEV cleavage site

<400> SEQUENCE: 3

```
Glu Asn Leu Tyr Phe Gln Gly
1               5
```

<210> SEQ ID NO 4
<211> LENGTH: 21
<212> TYPE: DNA
<213> ORGANISM: Artificial Sequence
<220> FEATURE:
<223> OTHER INFORMATION: nucleotide sequence of a TEV cleavage site

<400> SEQUENCE: 4

```
gaaaacctgt attttcaggg a                                               21
```

<210> SEQ ID NO 5
<211> LENGTH: 7
<212> TYPE: PRT
<213> ORGANISM: Artificial Sequence
<220> FEATURE:
<223> OTHER INFORMATION: amino acid sequence of another TEV cleavage
      site

<400> SEQUENCE: 5

```
Glu Asn Leu Tyr Phe Gln Ser
1               5
```

<210> SEQ ID NO 6
<211> LENGTH: 21
<212> TYPE: DNA
<213> ORGANISM: Artificial Sequence
<220> FEATURE:
<223> OTHER INFORMATION: nucleotide sequence of another TEV cleavage
      site

<400> SEQUENCE: 6

```
gaaaacctgt attttcagtc t                                               21
```

<210> SEQ ID NO 7
<211> LENGTH: 86
<212> TYPE: PRT
<213> ORGANISM: Artificial Sequence
<220> FEATURE:
<223> OTHER INFORMATION: precursor protein (prolispro) of human insulin
      analog lispro

<400> SEQUENCE: 7

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85
```

<210> SEQ ID NO 8
<211> LENGTH: 258
<212> TYPE: DNA
<213> ORGANISM: Artificial Sequence
<220> FEATURE:
<223> OTHER INFORMATION: prolispro nucleotide sequence

<400> SEQUENCE: 8

```
ttcgttaacc aacacctgtg cggcagccac ctggtagagg cactgtatct ggtttgtggt      60
gaacgtggct tcttctatac taaaccgact cgtcgcgaag cagaggatct gcaagtgggt     120
caggttgagc tgggcggtgg tccgggtgct ggctccctgc aaccgctggc gctggagggt     180
tccctgcaaa agcgtggtat cgtggaacag tgttgcactt ctatttgctc tctgtatcag     240
ctggaaaatt actgtaat                                                   258
```

<210> SEQ ID NO 9
<211> LENGTH: 345
<212> TYPE: PRT
<213> ORGANISM: Artificial Sequence
<220> FEATURE:
<223> OTHER INFORMATION: prolispro-sfGFP fusion protein sequence

<400> SEQUENCE: 9

```
Met Ala Arg Phe Val Asn Gln His Leu Cys Gly Ser His Leu Val Glu
1               5                   10                  15

Ala Leu Tyr Leu Val Cys Gly Glu Arg Gly Phe Phe Tyr Thr Lys Pro
            20                  25                  30

Thr Arg Arg Glu Ala Glu Asp Leu Gln Val Gly Gln Val Glu Leu Gly
        35                  40                  45

Gly Gly Pro Gly Ala Gly Ser Leu Gln Pro Leu Ala Leu Glu Gly Ser
    50                  55                  60

Leu Gln Lys Arg Gly Ile Val Glu Gln Cys Cys Thr Ser Ile Cys Ser
65                  70                  75                  80

Leu Tyr Gln Leu Glu Asn Tyr Cys Asn Arg Glu Asn Leu Tyr Phe Gln
                85                  90                  95

Gly Ala Met Val Ser Lys Gly Glu Glu Leu Phe Thr Gly Val Val Pro
            100                 105                 110
```

Ile Leu Val Glu Leu Asp Gly Asp Val Asn Gly His Lys Phe Ser Val
         115                 120                 125
Arg Gly Glu Gly Glu Gly Asp Ala Thr Asn Gly Lys Leu Thr Leu Lys
     130                 135                 140
Phe Ile Cys Thr Thr Gly Lys Leu Pro Val Pro Trp Pro Thr Leu Val
145                 150                 155                 160
Thr Thr Leu Thr Tyr Gly Val Gln Cys Phe Ser Arg Tyr Pro Asp His
             165                 170                 175
Met Lys Arg His Asp Phe Phe Lys Ser Ala Met Pro Glu Gly Tyr Val
         180                 185                 190
Gln Glu Arg Thr Ile Ser Phe Lys Asp Asp Gly Thr Tyr Lys Thr Arg
     195                 200                 205
Ala Glu Val Lys Phe Glu Gly Asp Thr Leu Val Asn Arg Ile Glu Leu
 210                 215                 220
Lys Gly Ile Asp Phe Lys Glu Asp Gly Asn Ile Leu Gly His Lys Leu
225                 230                 235                 240
Glu Tyr Asn Phe Asn Ser His Asn Val Tyr Ile Thr Ala Asp Lys Gln
             245                 250                 255
Lys Asn Gly Ile Lys Ala Asn Phe Lys Ile Arg His Asn Val Glu Asp
         260                 265                 270
Gly Ser Val Gln Leu Ala Asp His Tyr Gln Gln Asn Thr Pro Ile Gly
     275                 280                 285
Asp Gly Pro Val Leu Leu Pro Asp Asn His Tyr Leu Ser Thr Gln Ser
 290                 295                 300
Val Leu Ser Lys Asp Pro Asn Glu Lys Arg Asp His Met Val Leu Leu
305                 310                 315                 320
Glu Phe Val Thr Ala Ala Gly Ile Thr His Gly Met Asp Glu Leu Tyr
             325                 330                 335
Lys Gly Ser His His His His His His
         340                 345

<210> SEQ ID NO 10
<211> LENGTH: 1035
<212> TYPE: DNA
<213> ORGANISM: Artificial Sequence
<220> FEATURE:
<223> OTHER INFORMATION: prolispro-sfGFP fusion protein nucleotide
      sequence

<400> SEQUENCE: 10
atggcgcgtt tcgttaacca acacctgtgc ggcagccacc tggtagaggc actgtatctg      60
gtttgtggtg aacgtggctt cttctatact aaaccgactc gtcgcgaagc agaggatctg     120
caagtgggtc aggttgagct gggcggtggt ccgggtgctg ctccctgca accgctggcg      180 ctggagggtt ccctgcaaaa gcgtggtatc gtggaacagt gttgcacttc tatttgctct     240
ctgtatcagc tggaaaatta ctgtaatcgt gaaaacctgt attttcaggg agccatggtt     300
tctaaaggtg aagaactttt tactggtgtt gttcctattc ttgttgaact tgatggtgat     360
gttaatggtc ataaattttc tgttcgtggt gaaggtgaag gtgatgctac taatggtaaa     420
cttactctta aatttatttg tactactggt aaacttcctg ttccttggcc tactcttgtt     480
actactctta cttatggtgt tcaatgtttt tctcgttatc ctgatcatat gaaacgtcat     540
gattttttta atctgctat gcctgaaggt tatgttcaag aacgtactat ttctttaaa      600 gatgatggta cttataaaac tcgtgctgaa gttaaatttg aaggtgatac tcttgttaat     660

| | | |
|---|---|---|
| cgtattgaac ttaaaggtat tgattttaaa gaagatggta atattcttgg tcataaactt | 720 | |
| gaatataatt ttaattctca taatgtttat attactgctg ataaacaaaa aaatggtatt | 780 | |
| aaagctaatt ttaaaattcg tcataatgtt gaagatggtt ctgttcaact tgctgatcat | 840 | |
| tatcaacaaa atactcctat tggtgatggt cctgttcttc ttcctgataa tcattatctt | 900 | |
| tctactcaat ctgttctttc taaagatcct aatgaaaaac gtgatcatat ggttcttctt | 960 | |
| gaatttgtta ctgctgctgg tattactcat ggtatggatg aactttataa aggttctcat | 1020 | |
| catcatcatc atcat | 1035 | |

```
<210> SEQ ID NO 11
<211> LENGTH: 86
<212> TYPE: PRT
<213> ORGANISM: Homo sapiens

<400> SEQUENCE: 11
```

Phe Val Asn Gln His Leu Cys Gly Ser His Leu Val Glu Ala Leu Tyr
1               5                  10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

```
<210> SEQ ID NO 12
<211> LENGTH: 258
<212> TYPE: DNA
<213> ORGANISM: Homo sapiens

<400> SEQUENCE: 12
```

| | | |
|---|---|---|
| ttcgttaacc aacacctgtg cggcagccac ctggtagagg cactgtatct ggtttgtggt | 60 | |
| gaacgtggct tcttctatac tccgaaaact cgtcgcgaag cagaggatct gcaagtgggt | 120 | |
| caggttgagc tgggcggtgg tccgggtgct ggctccctgc aaccgctggc gctggagggt | 180 | |
| tccctgcaaa agcgtggtat cgtggaacag tgttgcactt ctatttgctc tctgtatcag | 240 | |
| ctggaaaatt actgtaat | 258 | |

```
<210> SEQ ID NO 13
<211> LENGTH: 345
<212> TYPE: PRT
<213> ORGANISM: Artificial Sequence
<220> FEATURE:
<223> OTHER INFORMATION: proinsulin-sfGFP fusion protein amino acid
      sequence

<400> SEQUENCE: 13
```

Met Ala Arg Phe Val Asn Gln His Leu Cys Gly Ser His Leu Val Glu
1               5                  10                  15

Ala Leu Tyr Leu Val Cys Gly Glu Arg Gly Phe Phe Tyr Thr Pro Lys
            20                  25                  30

Thr Arg Arg Glu Ala Glu Asp Leu Gln Val Gly Gln Val Glu Leu Gly
        35                  40                  45

Gly Gly Pro Gly Ala Gly Ser Leu Gln Pro Leu Ala Leu Glu Gly Ser

```
            50                  55                  60
Leu Gln Lys Arg Gly Ile Val Glu Gln Cys Cys Thr Ser Ile Cys Ser
 65                  70                  75                  80

Leu Tyr Gln Leu Glu Asn Tyr Cys Asn Arg Glu Asn Leu Tyr Phe Gln
                 85                  90                  95

Gly Ala Met Val Ser Lys Gly Glu Glu Leu Phe Thr Gly Val Val Pro
            100                 105                 110

Ile Leu Val Glu Leu Asp Gly Asp Val Asn Gly His Lys Phe Ser Val
                115                 120                 125

Arg Gly Glu Gly Glu Gly Asp Ala Thr Asn Gly Lys Leu Thr Leu Lys
            130                 135                 140

Phe Ile Cys Thr Thr Gly Lys Leu Pro Val Pro Trp Pro Thr Leu Val
145                 150                 155                 160

Thr Thr Leu Thr Tyr Gly Val Gln Cys Phe Ser Arg Tyr Pro Asp His
                165                 170                 175

Met Lys Arg His Asp Phe Phe Lys Ser Ala Met Pro Glu Gly Tyr Val
            180                 185                 190

Gln Glu Arg Thr Ile Ser Phe Lys Asp Asp Gly Thr Tyr Lys Thr Arg
                195                 200                 205

Ala Glu Val Lys Phe Glu Gly Asp Thr Leu Val Asn Arg Ile Glu Leu
            210                 215                 220

Lys Gly Ile Asp Phe Lys Glu Asp Gly Asn Ile Leu Gly His Lys Leu
225                 230                 235                 240

Glu Tyr Asn Phe Asn Ser His Asn Val Tyr Ile Thr Ala Asp Lys Gln
                245                 250                 255

Lys Asn Gly Ile Lys Ala Asn Phe Lys Ile Arg His Asn Val Glu Asp
            260                 265                 270

Gly Ser Val Gln Leu Ala Asp His Tyr Gln Gln Asn Thr Pro Ile Gly
                275                 280                 285

Asp Gly Pro Val Leu Leu Pro Asp Asn His Tyr Leu Ser Thr Gln Ser
            290                 295                 300

Val Leu Ser Lys Asp Pro Asn Glu Lys Arg Asp His Met Val Leu Leu
305                 310                 315                 320

Glu Phe Val Thr Ala Ala Gly Ile Thr His Gly Met Asp Glu Leu Tyr
                325                 330                 335

Lys Gly Ser His His His His His
            340                 345

<210> SEQ ID NO 14
<211> LENGTH: 1035
<212> TYPE: DNA
<213> ORGANISM: Artificial Sequence
<220> FEATURE:
<223> OTHER INFORMATION: proinsulin-sfGFP fusion protein nucleotide
      sequence

<400> SEQUENCE: 14
atggcgcgtt tcgttaacca acacctgtgc ggcagccacc tggtagaggc actgtatctg      60
gtttgtggtg aacgtggctt cttctatact ccgaaaactc gtcgcgaagc agaggatctg     120
caagtgggtc aggttgagct gggcggtggt ccgggtgctg gctccctgca accgctggcg     180
ctggagggtt ccctgcaaaa gcgtggtatc gtggaacagt gttgcacttc tatttgctct     240
ctgtatcagc tggaaaatta ctgtaatcgt gaaaacctgt attttcaggg agccatggtt     300
tctaaaggtg aagaactttt tactggtgtt gttcctattc tcgttgaact tgatggtgat     360
```

```
gttaatggtc ataaattttc tgttcgtggt gaaggtgaag gtgatgctac taatggtaaa    420
cttactctta aatttatttg tactactggt aaacttcctg ttccttggcc tactcttgtt    480
actactctta cttatggtgt tcaatgtttt tctcgttatc ctgatcatat gaaacgtcat    540
gattttttta aatctgctat gcctgaaggt tatgttcaag aacgtactat ttcttttaaa    600
gatgatggta cttataaaac tcgtgctgaa gttaaatttg aaggtgatac tcttgttaat    660
cgtattgaac ttaaaggtat tgattttaaa gaagatggta atattcttgg tcataaactt    720
gaatataatt ttaattctca taatgtttat attactgctg ataaacaaaa aaatggtatt    780
aaagctaatt ttaaaattcg tcataatgtt gaagatggtt ctgttcaact tgctgatcat    840
tatcaacaaa atactcctat tggtgatggt cctgttcttc ttcctgataa tcattatctt    900
tctactcaat ctgttctttc taaagatcct aatgaaaaac gtgatcatat ggttcttctt    960
gaatttgtta ctgctgctgg tattactcat ggtatggatg aactttataa aggttctcat   1020
catcatcatc atcat                                                    1035
```

<210> SEQ ID NO 15
<211> LENGTH: 86
<212> TYPE: PRT
<213> ORGANISM: Artificial Sequence
<220> FEATURE:
<223> OTHER INFORMATION: precursor protein (proglargine) of human
      insulin analog glargine

<400> SEQUENCE: 15

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Gly
            85
```

<210> SEQ ID NO 16
<211> LENGTH: 258
<212> TYPE: DNA
<213> ORGANISM: Artificial Sequence
<220> FEATURE:
<223> OTHER INFORMATION: proglargine nucleotide sequence

<400> SEQUENCE: 16

```
ttcgttaacc aacacctgtg cggcagccac ctggtagagg cactgtatct ggtttgtggt     60
gaacgtggct tcttctatac tccgaaaact cgtcgcgaag cagaggatct gcaagtgggt    120
caggttgagc tgggcggtgg tccgggtgct ggctccctgc aaccgctggc gctggagggt    180
tccctgcaaa agcgtggtat cgtggaacag tgttgcactt ctatttgctc tctgtatcag    240
ctggaaaatt actgtggc                                                  258
```

<210> SEQ ID NO 17
<211> LENGTH: 345
<212> TYPE: PRT
<213> ORGANISM: Artificial Sequence
<220> FEATURE:

<223> OTHER INFORMATION: proglargine-sfGFP fusion protein amino acid
       sequence

<400> SEQUENCE: 17

Met Ala Arg Phe Val Asn Gln His Leu Cys Gly Ser His Leu Val Glu
1               5                   10                  15

Ala Leu Tyr Leu Val Cys Gly Glu Arg Gly Phe Phe Tyr Thr Pro Lys
            20                  25                  30

Thr Arg Arg Glu Ala Glu Asp Leu Gln Val Gly Gln Val Glu Leu Gly
        35                  40                  45

Gly Gly Pro Gly Ala Gly Ser Leu Gln Pro Leu Ala Leu Glu Gly Ser
    50                  55                  60

Leu Gln Lys Arg Gly Ile Val Glu Gln Cys Cys Thr Ser Ile Cys Ser
65                  70                  75                  80

Leu Tyr Gln Leu Glu Asn Tyr Cys Gly Arg Glu Asn Leu Tyr Phe Gln
                85                  90                  95

Gly Ala Met Val Ser Lys Gly Glu Glu Leu Phe Thr Gly Val Val Pro
            100                 105                 110

Ile Leu Val Glu Leu Asp Gly Asp Val Asn Gly His Lys Phe Ser Val
        115                 120                 125

Arg Gly Glu Gly Glu Gly Asp Ala Thr Asn Gly Lys Leu Thr Leu Lys
    130                 135                 140

Phe Ile Cys Thr Thr Gly Lys Leu Pro Val Pro Trp Pro Thr Leu Val
145                 150                 155                 160

Thr Thr Leu Thr Tyr Gly Val Gln Cys Phe Ser Arg Tyr Pro Asp His
                165                 170                 175

Met Lys Arg His Asp Phe Phe Lys Ser Ala Met Pro Glu Gly Tyr Val
            180                 185                 190

Gln Glu Arg Thr Ile Ser Phe Lys Asp Asp Gly Thr Tyr Lys Thr Arg
        195                 200                 205

Ala Glu Val Lys Phe Glu Gly Asp Thr Leu Val Asn Arg Ile Glu Leu
    210                 215                 220

Lys Gly Ile Asp Phe Lys Glu Asp Gly Asn Ile Leu Gly His Lys Leu
225                 230                 235                 240

Glu Tyr Asn Phe Asn Ser His Asn Val Tyr Ile Thr Ala Asp Lys Gln
                245                 250                 255

Lys Asn Gly Ile Lys Ala Asn Phe Lys Ile Arg His Asn Val Glu Asp
            260                 265                 270

Gly Ser Val Gln Leu Ala Asp His Tyr Gln Gln Asn Thr Pro Ile Gly
        275                 280                 285

Asp Gly Pro Val Leu Leu Pro Asp Asn His Tyr Leu Ser Thr Gln Ser
    290                 295                 300

Val Leu Ser Lys Asp Pro Asn Glu Lys Arg Asp His Met Val Leu Leu
305                 310                 315                 320

Glu Phe Val Thr Ala Ala Gly Ile Thr His Gly Met Asp Glu Leu Tyr
                325                 330                 335

Lys Gly Ser His His His His His His
            340                 345

<210> SEQ ID NO 18
<211> LENGTH: 1035
<212> TYPE: DNA
<213> ORGANISM: Artificial Sequence
<220> FEATURE:
<223> OTHER INFORMATION: proglargine-sfGFP fusion protein nucleotide
       sequence -continued

```
<400> SEQUENCE: 18
atggcgcgtt cgttaacca acacctgtgc ggcagccacc tggtagaggc actgtatctg      60
gtttgtggtg aacgtggctt cttctatact ccgaaaactc gtcgcgaagc agaggatctg    120
caagtgggtc aggttgagct gggcggtggt ccgggtgctg gctccctgca accgctggcg    180
ctggagggtt ccctgcaaaa gcgtggtatc gtggaacagt gttgcacttc tatttgctct    240
ctgtatcagc tggaaaatta ctgtggccgt gaaaacctgt attttcaggg agccatggtt    300
tctaaaggtg aagaactttt tactggtgtt gttcctattc ttgttgaact tgatggtgat    360
gttaatggtc ataaattttc tgttcgtggt gaaggtgaag gtgatgctac taatggtaaa    420
cttactctta aatttatttg tactactggt aaacttcctg ttccttggcc tactcttgtt    480
actactctta cttatggtgt tcaatgtttt tctcgttatc ctgatcatat gaaacgtcat    540 gatttttta aatctgctat gcctgaaggt tatgttcaag aacgtactat ttctttttaaa    600 gatgatggta cttataaaac tcgtgctgaa gttaaatttg aaggtgatac tcttgttaat    660
cgtattgaac ttaaaggtat tgattttaaa gaagatggta atattcttgg tcataaactt    720
gaatataatt ttaattctca taatgtttat attactgctg ataaacaaaa aaatggtatt    780
aaagctaatt ttaaaattcg tcataatgtt gaagatggtt ctgttcaact tgctgatcat    840
tatcaacaaa atactcctat tggtgatggt cctgttcttc ttcctgataa tcattatctt    900
tctactcaat ctgttctttc taaagatcct aatgaaaaac gtgatcatat ggttcttctt    960
gaatttgtta ctgctgctgg tattactcat ggtatggatg aactttataa aggttctcat   1020
catcatcatc atcat                                                    1035

<210> SEQ ID NO 19
<211> LENGTH: 34
<212> TYPE: PRT
<213> ORGANISM: Artificial Sequence
<220> FEATURE:
<223> OTHER INFORMATION: parathyroid hormone (PTH) protein sequence

<400> SEQUENCE: 19

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 20
<211> LENGTH: 102
<212> TYPE: DNA
<213> ORGANISM: Artificial Sequence
<220> FEATURE:
<223> OTHER INFORMATION: parathyroid hormone (PTH) nucleotide sequence

<400> SEQUENCE: 20
tctgtttctg aaatccagct gatgcacaac ctgggtaaac acctgaactc tatggaacgt     60
gttgaatggc tgcgtaaaaa actgcaggac gttcacaact tc                       102

<210> SEQ ID NO 21
<211> LENGTH: 290
<212> TYPE: PRT
<213> ORGANISM: Artificial Sequence
<220> FEATURE:
<223> OTHER INFORMATION: sfGFP-PTH fusion protein amino acid sequence
```

<400> SEQUENCE: 21

```
Met Val His His His His His Ala Ala Ser Lys Gly Glu Glu Leu
1               5                   10                  15

Phe Thr Gly Val Val Pro Ile Leu Val Glu Leu Asp Gly Asp Val Asn
            20                  25                  30

Gly His Lys Phe Ser Val Arg Gly Glu Gly Glu Gly Asp Ala Thr Asn
        35                  40                  45

Gly Lys Leu Thr Leu Lys Phe Ile Cys Thr Thr Gly Lys Leu Pro Val
    50                  55                  60

Pro Trp Pro Thr Leu Val Thr Thr Leu Thr Tyr Gly Val Gln Cys Phe
65              70                  75                  80

Ser Arg Tyr Pro Asp His Met Lys Arg His Asp Phe Phe Lys Ser Ala
                85                  90                  95

Met Pro Glu Gly Tyr Val Gln Glu Arg Thr Ile Ser Phe Lys Asp Asp
            100                 105                 110

Gly Thr Tyr Lys Thr Arg Ala Glu Val Lys Phe Glu Gly Asp Thr Leu
        115                 120                 125

Val Asn Arg Ile Glu Leu Lys Gly Ile Asp Phe Lys Glu Asp Gly Asn
    130                 135                 140

Ile Leu Gly His Lys Leu Glu Tyr Asn Phe Asn Ser His Asn Val Tyr
145                 150                 155                 160

Ile Thr Ala Asp Lys Gln Lys Asn Gly Ile Lys Ala Asn Phe Lys Ile
                165                 170                 175

Arg His Asn Val Glu Asp Gly Ser Val Gln Leu Ala Asp His Tyr Gln
            180                 185                 190

Gln Asn Thr Pro Ile Gly Asp Gly Pro Val Leu Leu Pro Asp Asn His
        195                 200                 205

Tyr Leu Ser Thr Gln Ser Val Leu Ser Lys Asp Pro Asn Glu Lys Arg
    210                 215                 220

Asp His Met Val Leu Leu Glu Phe Val Thr Ala Ala Gly Ile Thr His
225                 230                 235                 240

Gly Met Asp Glu Leu Tyr Lys Ala Arg Asp Glu Asn Leu Tyr Phe Gln
                245                 250                 255

Ser Val Ser Glu Ile Gln Leu Met His Asn Leu Gly Lys His Leu Asn
            260                 265                 270

Ser Met Glu Arg Val Glu Trp Leu Arg Lys Lys Leu Gln Asp Val His
        275                 280                 285

Asn Phe
    290
```

<210> SEQ ID NO 22
<211> LENGTH: 870
<212> TYPE: DNA
<213> ORGANISM: Artificial Sequence
<220> FEATURE:
<223> OTHER INFORMATION: sfGFP-PTH fusion protein nucleotide sequence

<400> SEQUENCE: 22

```
atggttcacc atcatcatca ccatgcggcg agcaaaggtg aagaactgtt taccggcgtt      60
gtgccgattc tggtggaact ggatggtgat gtgaatggcc ataaatttag cgttcgtggc     120
gaaggcgaag gtgatgcgac caacggtaaa ctgaccctga atttatttg caccaccggt      180 aaactgccgg ttccgtggcc gaccctggtg accaccctga cctatggcgt tcagtgcttt     240
agccgctatc cggatcatat gaaacgccat gatttcttta aaagcgcgat gccggaaggc     300
```

```
tatgtgcagg aacgtaccat tagcttcaaa gatgatggca cctataaaac ccgtgcggaa    360
gttaaatttg aaggcgatac cctggtgaac cgcattgaac tgaaaggtat tgattttaaa    420
gaagatggca acattctggg tcataaactg aatataatt tcaacagcca taatgtgtat    480
attaccgccg ataaacagaa aaatggcatc aaagcgaact ttaaaatccg tcacaacgtg    540
gaagatggta gcgtgcagct ggcggatcat tatcagcaga ataccccgat tggtgatggc    600
ccggtgctgc tgccggataa tcattatctg agcacccaga gcgttctgag caaagatccg    660
aatgaaaaac gtgatcatat ggtgctgctg gaatttgtta ccgccgcggg cattacccac    720
ggtatggatg aactgtataa agctcgagat gaaaacctgt attttcagtc tgtttctgaa    780
atccagctga tgcacaacct gggtaaacac ctgaactcta tggaacgtgt tgaatggctg    840
cgtaaaaaac tgcaggacgt tcacaacttc                                     870

<210> SEQ ID NO 23
<211> LENGTH: 32
<212> TYPE: PRT
<213> ORGANISM: Artificial Sequence
<220> FEATURE:
<223> OTHER INFORMATION: salmon calcitonin protein sequence

<400> SEQUENCE: 23

Cys Ser Asn Leu Ser Thr Cys Val Leu Gly Lys Leu Ser Gln Glu Leu
 1               5                  10                  15

His Lys Leu Gln Thr Tyr Pro Arg Thr Asn Thr Gly Ser Gly Thr Pro
                20                  25                  30

<210> SEQ ID NO 24
<211> LENGTH: 96
<212> TYPE: DNA
<213> ORGANISM: Artificial Sequence
<220> FEATURE:
<223> OTHER INFORMATION: salmon calcitonin nucleotide sequence

<400> SEQUENCE: 24
tgctctgcgc tgtctacctg cgttctgggt ctgctgtctg gtggtctgca cctgctgggt    60 accacccegg cgaccgcgac cggttctggt accccg                              96

<210> SEQ ID NO 25
<211> LENGTH: 288
<212> TYPE: PRT
<213> ORGANISM: Artificial Sequence
<220> FEATURE:
<223> OTHER INFORMATION: sfGFP-calcitonin amino acid sequence

<400> SEQUENCE: 25

Met Val His His His His His His Ala Ala Ser Lys Gly Glu Glu Leu
 1               5                  10                  15

Phe Thr Gly Val Val Pro Ile Leu Val Glu Leu Asp Gly Asp Val Asn
                20                  25                  30

Gly His Lys Phe Ser Val Arg Gly Glu Gly Glu Gly Asp Ala Thr Asn
            35                  40                  45

Gly Lys Leu Thr Leu Lys Phe Ile Cys Thr Thr Gly Lys Leu Pro Val
        50                  55                  60

Pro Trp Pro Thr Leu Val Thr Thr Leu Thr Tyr Gly Val Gln Cys Phe
65                  70                  75                  80

Ser Arg Tyr Pro Asp His Met Lys Arg His Asp Phe Phe Lys Ser Ala
                85                  90                  95

Met Pro Glu Gly Tyr Val Gln Glu Arg Thr Ile Ser Phe Lys Asp Asp
```

```
                     100                 105                 110
Gly Thr Tyr Lys Thr Arg Ala Glu Val Lys Phe Glu Gly Asp Thr Leu
                115                 120                 125

Val Asn Arg Ile Glu Leu Lys Gly Ile Asp Phe Lys Glu Asp Gly Asn
            130                 135                 140

Ile Leu Gly His Lys Leu Glu Tyr Asn Phe Asn Ser His Asn Val Tyr
145                 150                 155                 160

Ile Thr Ala Asp Lys Gln Lys Asn Gly Ile Lys Ala Asn Phe Lys Ile
                165                 170                 175

Arg His Asn Val Glu Asp Gly Ser Val Gln Leu Ala Asp His Tyr Gln
            180                 185                 190

Gln Asn Thr Pro Ile Gly Asp Gly Pro Val Leu Leu Pro Asp Asn His
        195                 200                 205

Tyr Leu Ser Thr Gln Ser Val Leu Ser Lys Asp Pro Asn Glu Lys Arg
210                 215                 220

Asp His Met Val Leu Leu Glu Phe Val Thr Ala Ala Gly Ile Thr His
225                 230                 235                 240

Gly Met Asp Glu Leu Tyr Lys Ala Arg Asp Glu Asn Leu Tyr Phe Gln
                245                 250                 255

Cys Ser Ala Leu Ser Thr Cys Val Leu Gly Leu Leu Ser Gly Leu
                260                 265                 270

His Leu Leu Gly Thr Thr Pro Ala Thr Ala Thr Gly Ser Gly Thr Pro
            275                 280                 285

<210> SEQ ID NO 26
<211> LENGTH: 864
<212> TYPE: DNA
<213> ORGANISM: Artificial Sequence
<220> FEATURE:
<223> OTHER INFORMATION: sfGFP-calcitonin nucleotide sequence

<400> SEQUENCE: 26
atggttcacc atcatcatca ccatgcggcg agcaaaggtg aagaactgtt taccggcgtt      60
gtgccgattc tggtggaact ggatggtgat gtgaatggcc ataaatttag cgttcgtggc     120
gaaggcgaag gtgatgcgac caacggtaaa ctgaccctga atttatttg caccaccggt     180 aaactgccgg ttccgtggcc gaccctggtg accaccctga cctatggcgt tcagtgcttt     240
agccgctatc cggatcatat gaaacgccat gatttcttta aaagcgcgat gccggaaggc     300
tatgtgcagg aacgtaccat tagcttcaaa gatgatggca cctataaaac ccgtgcggaa     360
gttaaatttg aaggcgatac cctggtgaac cgcattgaac tgaaaggtat tgattttaaa     420
gaagatggca acattctggg tcataaactg gaatataatt tcaacagcca taatgtgtat     480
attaccgccg ataaacagaa aaatggcatc aaagcgaact taaaatccg tcacaacgtg     540 gaagatggta gcgtgcagct ggcggatcat tatcagcaga taccccgat ggtgatggc     600 ccggtgctgc tgccggataa tcattatctg agcacccaga gcgttctgag caaagatccg     660
aatgaaaaac gtgatcatat ggtgctgctg gaatttgtta ccgccgcggg cattacccac     720
ggtatggatg aactgtataa agctcgagat gaaaacctgt attttcagtg ctctgcgctg     780
tctacctgcg ttctgggtct gctgtctggt ggtctgcacc tgctgggtac caccccggcg     840
accgcgaccg gttctggtac cccg                                              864

<210> SEQ ID NO 27
<211> LENGTH: 39
<212> TYPE: PRT
```

<213> ORGANISM: Artificial Sequence
<220> FEATURE:
<223> OTHER INFORMATION: glucagon-like peptide-1 (GLP-1) protein
     sequence

<400> SEQUENCE: 27

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 28
<211> LENGTH: 117
<212> TYPE: DNA
<213> ORGANISM: Artificial Sequence
<220> FEATURE:
<223> OTHER INFORMATION: GLP-1 nucleotide sequence

<400> SEQUENCE: 28
cacggtggtg gtaccccgac ctctgcgctg tctctgggta tgggtggtgg tgcggttgcg     60
ctgccgatcg gtaccctgct ggcgggtggt ccgtcttctg gtgcgccgcc gccgtct      117

<210> SEQ ID NO 29
<211> LENGTH: 295
<212> TYPE: PRT
<213> ORGANISM: Artificial Sequence
<220> FEATURE:
<223> OTHER INFORMATION: sfGFP-GLP-1 amino acid sequence

<400> SEQUENCE: 29

Met Val His His His His His His Ala Ala Ser Lys Gly Glu Glu Leu
1               5                   10                  15

Phe Thr Gly Val Val Pro Ile Leu Val Glu Leu Asp Gly Asp Val Asn
            20                  25                  30

Gly His Lys Phe Ser Val Arg Gly Glu Gly Glu Gly Asp Ala Thr Asn
        35                  40                  45

Gly Lys Leu Thr Leu Lys Phe Ile Cys Thr Thr Gly Lys Leu Pro Val
    50                  55                  60

Pro Trp Pro Thr Leu Val Thr Thr Leu Thr Tyr Gly Val Gln Cys Phe
65                  70                  75                  80

Ser Arg Tyr Pro Asp His Met Lys Arg His Asp Phe Phe Lys Ser Ala
                85                  90                  95

Met Pro Glu Gly Tyr Val Gln Glu Arg Thr Ile Ser Phe Lys Asp Asp
            100                 105                 110

Gly Thr Tyr Lys Thr Arg Ala Glu Val Lys Phe Glu Gly Asp Thr Leu
        115                 120                 125

Val Asn Arg Ile Glu Leu Lys Gly Ile Asp Phe Lys Glu Asp Gly Asn
    130                 135                 140

Ile Leu Gly His Lys Leu Glu Tyr Asn Phe Asn Ser His Asn Val Tyr
145                 150                 155                 160

Ile Thr Ala Asp Lys Gln Lys Asn Gly Ile Lys Ala Asn Phe Lys Ile
                165                 170                 175

Arg His Asn Val Glu Asp Gly Ser Val Gln Leu Ala Asp His Tyr Gln
            180                 185                 190

Gln Asn Thr Pro Ile Gly Asp Gly Pro Val Leu Leu Pro Asp Asn His
        195                 200                 205

```
Tyr Leu Ser Thr Gln Ser Val Leu Ser Lys Asp Pro Asn Glu Lys Arg
        210                 215                 220
Asp His Met Val Leu Leu Glu Phe Val Thr Ala Ala Gly Ile Thr His
225                 230                 235                 240
Gly Met Asp Glu Leu Tyr Lys Ala Arg Asp Glu Asn Leu Tyr Phe Gln
                245                 250                 255
His Gly Gly Gly Thr Pro Thr Ser Ala Leu Ser Leu Gly Met Gly
            260                 265                 270
Gly Ala Val Ala Leu Pro Ile Gly Thr Leu Leu Ala Gly Gly Pro Ser
        275                 280                 285
Ser Gly Ala Pro Pro Pro Ser
        290                 295

<210> SEQ ID NO 30
<211> LENGTH: 885
<212> TYPE: DNA
<213> ORGANISM: Artificial Sequence
<220> FEATURE:
<223> OTHER INFORMATION: sfGFP-GLP-1 nucleotide sequence

<400> SEQUENCE: 30
atggttcacc atcatcatca ccatgcggcg agcaaaggtg aagaactgtt taccggcgtt    60
gtgccgattc tggtggaact ggatggtgat gtgaatggcc ataaatttag cgttcgtggc   120
gaaggcgaag tgatgcgac caacggtaaa ctgaccctga atttatttg caccaccggt   180
aaactgccgg ttccgtggcc gaccctggtg accaccctga cctatggcgt tcagtgcttt   240
agccgctatc cggatcatat gaaacgccat gatttcttta aaagcgcgat gccggaaggc   300
tatgtgcagg aacgtaccat tagcttcaaa gatgatggca cctataaaac ccgtgcggaa   360
gttaaatttg aaggcgatac cctggtgaac cgcattgaac tgaaaggtat tgattttaaa   420
gaagatggca acattctggg tcataaactg gaatataatt tcaacagcca taatgtgtat   480
attaccgccg ataaacagaa aaatggcatc aaagcgaact ttaaaatccg tcacaacgtg   540
gaagatggta gcgtgcagct ggcggatcat tatcagcaga taccccgat tggtgatggc   600
ccggtgctgc tgccggataa tcattatctg agcacccaga gcgttctgag caaagatccg   660
aatgaaaaac gtgatcatat ggtgctgctg gaatttgtta ccgccgcggg cattacccac   720
ggtatggatg aactgtataa agctcgagat gaaaacctgt attttcagca cggtggtggt   780
acccccgacct ctgcgctgtc tctgggtatg ggtggtggtg cggttgcgct gccgatcggt   840
accctgctgg cgggtggtcc gtcttctggt gcgccgccgc cgtct                    885

<210> SEQ ID NO 31
<211> LENGTH: 5
<212> TYPE: PRT
<213> ORGANISM: Artificial Sequence
<220> FEATURE:
<223> OTHER INFORMATION: Artificial peptide

<400> SEQUENCE: 31

Asp Met Gln Asp Ile
1               5

<210> SEQ ID NO 32
<211> LENGTH: 5
<212> TYPE: PRT
<213> ORGANISM: Artificial Sequence
<220> FEATURE:
<223> OTHER INFORMATION: Artificial peptide
```

```
<400> SEQUENCE: 32

Asp Glu Val Asp Ile
1               5

<210> SEQ ID NO 33
<211> LENGTH: 5
<212> TYPE: PRT
<213> ORGANISM: Artificial Sequence
<220> FEATURE:
<223> OTHER INFORMATION: Artificial peptide

<400> SEQUENCE: 33

Leu Glu Val Asp Ile
1               5

<210> SEQ ID NO 34
<211> LENGTH: 5
<212> TYPE: PRT
<213> ORGANISM: Artificial Sequence
<220> FEATURE:
<223> OTHER INFORMATION: Artificial peptide

<400> SEQUENCE: 34

Trp Glu His Asp Ile
1               5

<210> SEQ ID NO 35
<211> LENGTH: 5
<212> TYPE: PRT
<213> ORGANISM: Artificial Sequence
<220> FEATURE:
<223> OTHER INFORMATION: Artificial peptide

<400> SEQUENCE: 35

Leu Glu His Asp Ile
1               5

<210> SEQ ID NO 36
<211> LENGTH: 5
<212> TYPE: PRT
<213> ORGANISM: Artificial Sequence
<220> FEATURE:
<223> OTHER INFORMATION: Artificial peptide

<400> SEQUENCE: 36

Val Glu Ile Asp Ile
1               5

<210> SEQ ID NO 37
<211> LENGTH: 5
<212> TYPE: PRT
<213> ORGANISM: Artificial Sequence
<220> FEATURE:
<223> OTHER INFORMATION: Artificial peptide

<400> SEQUENCE: 37

Val Glu His Asp Ile
1               5

<210> SEQ ID NO 38
<211> LENGTH: 5
<212> TYPE: PRT
<213> ORGANISM: Artificial Sequence
<220> FEATURE:
<223> OTHER INFORMATION: Artificial peptide

<400> SEQUENCE: 38
```

Ile Glu Thr Asp Ile
1               5

<210> SEQ ID NO 39
<211> LENGTH: 5
<212> TYPE: PRT
<213> ORGANISM: Artificial Sequence
<220> FEATURE:
<223> OTHER INFORMATION: Artificial peptide

<400> SEQUENCE: 39

Leu Glu Thr Asp Ile
1               5

<210> SEQ ID NO 40
<211> LENGTH: 5
<212> TYPE: PRT
<213> ORGANISM: Artificial Sequence
<220> FEATURE:
<223> OTHER INFORMATION: Artificial peptide

<400> SEQUENCE: 40

Ile Glu Ala Asp Ile
1               5

<210> SEQ ID NO 41
<211> LENGTH: 5
<212> TYPE: PRT
<213> ORGANISM: Artificial Sequence
<220> FEATURE:
<223> OTHER INFORMATION: Artificial peptide

<400> SEQUENCE: 41

Asp Asp Asp Asp Lys
1               5

<210> SEQ ID NO 42
<211> LENGTH: 4
<212> TYPE: PRT
<213> ORGANISM: Artificial Sequence
<220> FEATURE:
<223> OTHER INFORMATION: Artificial peptide

<400> SEQUENCE: 42

Arg Gly Glu Ile
1

<210> SEQ ID NO 43
<211> LENGTH: 4
<212> TYPE: PRT
<213> ORGANISM: Artificial Sequence
<220> FEATURE:
<223> OTHER INFORMATION: Artificial peptide

<400> SEQUENCE: 43

Arg Gly Asp Ile
1

<210> SEQ ID NO 44
<211> LENGTH: 4
<212> TYPE: PRT
<213> ORGANISM: Artificial Sequence
<220> FEATURE:
<223> OTHER INFORMATION: Artificial peptide

<400> SEQUENCE: 44

```
Arg Gly Asp Ile
1

<210> SEQ ID NO 45
<211> LENGTH: 4
<212> TYPE: PRT
<213> ORGANISM: Artificial Sequence
<220> FEATURE:
<223> OTHER INFORMATION: Artificial peptide

<400> SEQUENCE: 45

Arg Gly Asp Ala
1

<210> SEQ ID NO 46
<211> LENGTH: 5
<212> TYPE: PRT
<213> ORGANISM: Artificial Sequence
<220> FEATURE:
<223> OTHER INFORMATION: Artificial peptide

<400> SEQUENCE: 46

Ile Glu Pro Asp Ile
1               5

<210> SEQ ID NO 47
<211> LENGTH: 24
<212> TYPE: DNA
<213> ORGANISM: Artificial Sequence
<220> FEATURE:
<223> OTHER INFORMATION: Artificial polynucleotide

<400> SEQUENCE: 47
aattaaccat ggttagcaaa ggtg                                   24

<210> SEQ ID NO 48
<211> LENGTH: 47
<212> TYPE: DNA
<213> ORGANISM: Artificial Sequence
<220> FEATURE:
<223> OTHER INFORMATION: Artificial polynucleotide

<400> SEQUENCE: 48
gatctcgagc tttaatggtg atgatgatgg tggctgcctt tatacag           47

<210> SEQ ID NO 49
<211> LENGTH: 27
<212> TYPE: DNA
<213> ORGANISM: Artificial Sequence
<220> FEATURE:
<223> OTHER INFORMATION: Artificial polynucleotide

<400> SEQUENCE: 49
cctacctgac gcttttatc gcaactc                                 27

<210> SEQ ID NO 50
<211> LENGTH: 25
<212> TYPE: DNA
<213> ORGANISM: Artificial Sequence
<220> FEATURE:
<223> OTHER INFORMATION: Artificial polynucleotide

<400> SEQUENCE: 50
ggctgaaaat cttctctcat ccgcc                                  25

<210> SEQ ID NO 51
```

```
<211> LENGTH: 39
<212> TYPE: DNA
<213> ORGANISM: Artificial Sequence
<220> FEATURE:
<223> OTHER INFORMATION: Artificial polynucleotide

<400> SEQUENCE: 51
aaccatggtt caccatcatc atcaccatgc ggcgagcaa                                  39

<210> SEQ ID NO 52
<211> LENGTH: 28
<212> TYPE: DNA
<213> ORGANISM: Artificial Sequence
<220> FEATURE:
<223> OTHER INFORMATION: Artificial polynucleotide

<400> SEQUENCE: 52
atctcgagct ttatacagtt catccata                                             28

<210> SEQ ID NO 53
<211> LENGTH: 27
<212> TYPE: DNA
<213> ORGANISM: Artificial Sequence
<220> FEATURE:
<223> OTHER INFORMATION: Artificial polynucleotide

<400> SEQUENCE: 53
cctacctgac gcttttatc gcaactc                                               27

<210> SEQ ID NO 54
<211> LENGTH: 25
<212> TYPE: DNA
<213> ORGANISM: Artificial Sequence
<220> FEATURE:
<223> OTHER INFORMATION: Artificial polynucleotide

<400> SEQUENCE: 54
ggctgaaaat cttctctcat ccgcc                                                25

<210> SEQ ID NO 55
<211> LENGTH: 36
<212> TYPE: DNA
<213> ORGANISM: Artificial Sequence
<220> FEATURE:
<223> OTHER INFORMATION: Artificial polynucleotide

<400> SEQUENCE: 55
gaattaacca tggcgcgttt cgttaaccaa cacctg                                    36

<210> SEQ ID NO 56
<211> LENGTH: 49
<212> TYPE: DNA
<213> ORGANISM: Artificial Sequence
<220> FEATURE:
<223> OTHER INFORMATION: Artificial polynucleotide

<400> SEQUENCE: 56
aacccatggc tccctgaaaa tacaggtttt cacgattaca gtaattttc                      49

<210> SEQ ID NO 57
<211> LENGTH: 27
<212> TYPE: DNA
<213> ORGANISM: Artificial Sequence
<220> FEATURE:
<223> OTHER INFORMATION: Artificial polynucleotide

<400> SEQUENCE: 57
```

```
cctacctgac gcttttttatc gcaactc                                        27

<210> SEQ ID NO 58
<211> LENGTH: 25
<212> TYPE: DNA
<213> ORGANISM: Artificial Sequence
<220> FEATURE:
<223> OTHER INFORMATION: Artificial polynucleotide

<400> SEQUENCE: 58
ccgaaaactc gtcgcgaagc agagg                                           25

<210> SEQ ID NO 59
<211> LENGTH: 24
<212> TYPE: DNA
<213> ORGANISM: Artificial Sequence
<220> FEATURE:
<223> OTHER INFORMATION: Artificial polynucleotide

<400> SEQUENCE: 59
agtatagaag aagccacgtt cacc                                            24

<210> SEQ ID NO 60
<211> LENGTH: 27
<212> TYPE: DNA
<213> ORGANISM: Artificial Sequence
<220> FEATURE:
<223> OTHER INFORMATION: Artificial polynucleotide

<400> SEQUENCE: 60
cctacctgac gcttttttatc gcaactc                                        27

<210> SEQ ID NO 61
<211> LENGTH: 22
<212> TYPE: DNA
<213> ORGANISM: Artificial Sequence
<220> FEATURE:
<223> OTHER INFORMATION: Artificial polynucleotide

<400> SEQUENCE: 61
cgtgaaaacc tgtattttca gg                                              22

<210> SEQ ID NO 62
<211> LENGTH: 25
<212> TYPE: DNA
<213> ORGANISM: Artificial Sequence
<220> FEATURE:
<223> OTHER INFORMATION: Artificial polynucleotide

<400> SEQUENCE: 62
gccacagtaa ttttccagct tatac                                           25

<210> SEQ ID NO 63
<211> LENGTH: 27
<212> TYPE: DNA
<213> ORGANISM: Artificial Sequence
<220> FEATURE:
<223> OTHER INFORMATION: Artificial polynucleotide

<400> SEQUENCE: 63
cctacctgac gcttttttatc gcaactc                                        27

<210> SEQ ID NO 64
<211> LENGTH: 41
<212> TYPE: DNA
```

<213> ORGANISM: Artificial Sequence
<220> FEATURE:
<223> OTHER INFORMATION: Artificial polynucleotide

<400> SEQUENCE: 64
acctcgagat gaaaacctgt attttcagtc tgtttctgaa a                41

<210> SEQ ID NO 65
<211> LENGTH: 31
<212> TYPE: DNA
<213> ORGANISM: Artificial Sequence
<220> FEATURE:
<223> OTHER INFORMATION: Artificial polynucleotide

<400> SEQUENCE: 65
tctaattccc ttagaagttg ttaagctcct g                           31

<210> SEQ ID NO 66
<211> LENGTH: 25
<212> TYPE: DNA
<213> ORGANISM: Artificial Sequence
<220> FEATURE:
<223> OTHER INFORMATION: Artificial polynucleotide

<400> SEQUENCE: 66
ggctgaaaat cttctctcat ccgcc                                  25

<210> SEQ ID NO 67
<211> LENGTH: 42
<212> TYPE: DNA
<213> ORGANISM: Artificial Sequence
<220> FEATURE:
<223> OTHER INFORMATION: Artificial polynucleotide

<400> SEQUENCE: 67
agctcgagat gaaaacctgt attttcagtg ctctgcgctg tc               42

<210> SEQ ID NO 68
<211> LENGTH: 25
<212> TYPE: DNA
<213> ORGANISM: Artificial Sequence
<220> FEATURE:
<223> OTHER INFORMATION: Artificial polynucleotide

<400> SEQUENCE: 68
tcgaattccc ttacggggta ccaga                                  25

<210> SEQ ID NO 69
<211> LENGTH: 25
<212> TYPE: DNA
<213> ORGANISM: Artificial Sequence
<220> FEATURE:
<223> OTHER INFORMATION: Artificial polynucleotide

<400> SEQUENCE: 69
ggctgaaaat cttctctcat ccgcc                                  25

<210> SEQ ID NO 70
<211> LENGTH: 42
<212> TYPE: DNA
<213> ORGANISM: Artificial Sequence
<220> FEATURE:
<223> OTHER INFORMATION: Artificial polynucleotide

<400> SEQUENCE: 70
agctcgagat gaaaacctgt attttcagca cggtggtggt ac               42

```
<210> SEQ ID NO 71
<211> LENGTH: 31
<212> TYPE: DNA
<213> ORGANISM: Artificial Sequence
<220> FEATURE:
<223> OTHER INFORMATION: Artificial polynucleotide

<400> SEQUENCE: 71
tcgaattccc ttaagacggc ggcggcgcac c                              31

<210> SEQ ID NO 72
<211> LENGTH: 25
<212> TYPE: DNA
<213> ORGANISM: Artificial Sequence
<220> FEATURE:
<223> OTHER INFORMATION: Artificial polynucleotide

<400> SEQUENCE: 72
ggctgaaaat cttctctcat ccgcc                                     25
```

FUSION PROTEINS OF SUPERFOLDER GREEN FLUORESCENT PROTEIN AND USE THEREOF

RELATED APPLICATIONS

This application is a continuation of U.S. application Ser. No. 14/387,456, filed Sep. 23, 2014, now U.S. Pat. No. 9,714,274, which is a U.S. National Phase application of International Application No. PCT/US2013/033702, filed Mar. 25, 2013, which claims priority to, and the benefit of, U.S. provisional application No. 61/615,178, filed Mar. 23, 2012, the entire contents of each of which are incorporated herein by reference in their entireties.

INCORPORATION-BY-REFERENCE OF SEQUENCE LISTING

The contents of the text file named "WUPH-001 CO1US SEQ LISTING.txt," which was created on Apr. 19, 2018 and is 43 KB in size, are hereby incorporated by reference in their entireties.

FIELD OF THE INVENTION

The present invention generally pertains to recombinant peptides that contain less than 200 amino acid residues and one or more novel carrier proteins derived from superfolder green fluorescent protein or mutants thereof as well as methods of producing the recombinant peptides using novel carrier proteins derived from superfolder green fluorescent protein or its mutants.

BACKGROUND OF THE INVENTION

Peptides are a group of biomolecules that have been broadly used as reagents in many biomedical research areas, therapeutic drugs in the treatment of diseases, and diagnostic agents in detecting pathogens and biomarkers. Two methods are generally used to synthesize peptides. One is chemical synthesis and the other is the recombinant expression. Chemical synthesis has been used for the preparation of a variety of therapeutic peptides including corticorelin, parathyroid hormone (PTH), glucagon-like peptide-1 (GLP-1) and its analogs exenatide and liragultide, enfuvirtide, calcitonin, bivalirudin, ziconotide, sermorelin, somatorelin, secretin, teduglutide, and insulin. This method needs multiple condensation reactions of amino acid fragments to generate peptides and requires tedious protection, deprotection, and purification processes. So far, most of commercial peptides with few than 50 amino acid residues are manufactured in this way. Given the increasing demand for peptides in pharmaceutical industry and biomedical research, the prices of amino acid fragments used for chemical synthesis of peptides have been continuously ascending. Therefore, for daily used therapeutic peptide drugs such as GLP-1 analogs, it will be difficult to maintain their affordable prices in the future. Although chemical synthesis of a peptide with more than 50 amino acid residues is technically achievable, the low yields and the exceeding amount of organic waste generated during the synthesis make it economically unfavourable. So far, most of peptides with more than 50 amino acid residues are recombinantly expressed in cell hosts such as bacterial, yeast, insect, and mammalian cells. For many years, it has been a common practice to use fusion proteins for the expression of peptides. The readily available carrier proteins include glutathione-S-transferase (WO94/04688 and Ray et al., BioTechnology, 11, 64, 1993), ribulokinase (U.S. Pat. No. 5,206,154 and Callaway et al., Antimicrob. Agents & Chemo., 37, 1614-1919, 1993), gp-55 protein (Gram H. et al., Biotechnology, 12, 1017-1023, 1994), ketosteroid isomerase (Kuliopulos A. et al., J. Am. Chem. Soc., 116, 4599-4607, 1994), ubiquitin (Pilon A. et al., Biotecnol. Prog. 13, 374-379, 1997), bovine prochymosin (Hauht et al., Biotechnolo. Bioengineer., 7, 55-61, 1998), GB1 domain (Darrinm et al., Biochemistry, 41, 7267-7274, 2003), RNA-binding protein (Sharon M. et al., Protein Exp. And Purif, 24, 374-383, 2002), SH2 domain (Fairlie W. et al., Protein Exp. And Purif. 26, 171-178, 2002), cellulose binding domain, small ubiquitin-like modifier, intein, bactericidal/permeability-increase protein, carbonic anhydrase (U.S. Pat. No. 5,962,270 and WO97/29127), alpha-lactalbumin (WO95/27782), beta-glactosidase (Shen S., PNAS, 281, 4627-4631, 1984), and chloramphenicol acetyltransferase (Dykes C. et al., European Journal of Biochemistry, 174, 411-416, 1988). These fusion carriers have been selected for their relatively high expression levels and fast folding processes in host cells. Although useful, the final yields of peptides recombinantly expressed using fusion carrier proteins typically do not exceed 100 mg/L. In addition, current available fusion protein methods for peptide expression also have many technical problems especially for the production of peptides smaller than 50 amino acid residues (Vileghe et al., Drug Discovery Today, 15, 40-56, 2010).

It would be highly desirable to provide with a new carrier protein overcoming the limitations of other existing carrier proteins for the production of recombinant peptides.

BRIEF SUMMARY OF THE INVENTION

The present invention is based at least in part on the unexpected discovery that superfolder green fluorescent protein or a mutant thereof, when used as carrier protein, leads to high expression levels of recombinant peptides in inclusion bodies or cytoplasm of bacterial cells. Accordingly, one aspect of the present invention relates to a novel carrier protein for constructing stable expression systems for the production of recombinant peptides as fusion proteins. In particular, the carrier protein includes superfolder green fluorescent protein or a mutant thereof.

In one embodiment, the fusion proteins as produced are expressed in intact and stable forms. In one embodiment, the novel carrier protein is easily removed by convenient methods and does not complicate subsequent steps of peptide purification. In one embodiment of the invention, the desired peptides are targeted to form inclusion bodies by engineering the carrier protein of the present invention for protection against in-cell proteolytic degradation. In accordance with the present invention there is provided a fusion carrier protein for expressing a target peptide, said fusion carrier protein being derived from superfolder green fluorescent protein, or a mutant thereof, and consisting of 237 or more amino acids in length. Preferably, the fusion carrier protein has an amino acid sequence as set forth in Formula I:

$$T1\text{-}A1\text{-}T2 \qquad (I)$$

wherein
  T1 is absent, a Met, a His-tag or at least one peptidic cleavage site,
  A1 is superfolder green fluorescent protein,
  T2 is absent, a His-tag or at least one peptidic cleavage site, provided that at most one of T1 and T2 is absent.

In embodiments, A1 is superfolder green fluorescent protein having an amino acid sequence of Ser-Lys-Gly-Glu-Glu-Leu-Phe-Thr-Gly-Val-Val-Pro-Ile-Leu-Val-Glu-Leu-Asp-Gly-Asp-Val-Asn-Gly-His-Lys-Phe-Ser-Val-Arg-Gly-Glu-Gly-Glu-Gly-Asp-Ala-Thr-Asn-Gly-Lys-Leu-Thr-Leu-Lys-Phe-Ile-Cys-Thr-Thr-Gly-Lys-Leu-Pro-Val-Pro-Trp-Pro-Thr-Leu-Val-Thr-Thr-Leu-Thr-Tyr-Gly-Val-Gln-Cys-Phe-Ser-Arg-Tyr-Pro-Asp-His-Met-Lys-Arg-His-Asp-Phe-Phe-Lys-Ser-Ala-Met-Pro-Glu-Gly-Tyr-Val-Gln-Glu-Arg-Thr-Ile-Ser-Phe-Lys-Asp-Asp-Gly-Thr-Tyr-Lys-Thr-Arg-Ala-Glu-Val-Lys-Phe-Glu-Gly-Asp-Thr-Leu-Val-Asn-Arg-Ile-Glu-Leu-Lys-Gly-Ile-Asp-Phe-Lys-Glu-Asp-Gly-Asn-Ile-Leu-Gly-His-Lys-Leu-Glu-Tyr-Asn-Phe-Asn-Ser-His-Asn-Val-Tyr-Ile-Thr-Ala-Asp-Lys-Gln-Lys-Asn-Gly-Ile-Lys-Ala-Asn-Phe-Lys-Ile-Arg-His-Asn-Val-Glu-Asp-Gly-Ser-Val-Gln-Leu-Ala-Asp-His-Tyr-Gln-Gln-Asn-Thr-Pro-Ile-Gly-Asp-Gly-Pro-Val-Leu-Leu-Pro-Asp-Asn-His-Tyr-Leu-Ser-Thr-Gln-Ser-Val-Leu-Ser-Lys-Asp-Pro-Asn-Glu-Lys-Arg-Asp-His-Met-Val-Leu-Leu-Glu-Phe-Val-Thr-Ala-Ala-Gly-Ile-Thr-His-Gly-Met-Asp-Glu-Leu-Tyr-Lys (SEQ ID NO:1), or an amino acid sequence that is at least 80%, at least 90%, at least 95%, at least 97%, or at least 99% identical to SEQ ID NO:1.

The peptidic cleavage site can be selected for example from the group consisting of Met, Cys, Pro, Asn, Glu, Tyr, Trp, Lys, Arg, Asn-Gly, Asp-Met-Gln-Asp-Ile (SEQ ID NO:31), Asp-Glu-Val-Asp-Ile (SEQ ID NO:32), Leu-Glu-Val-Asp-Ile (SEQ ID NO:33), Trp-Glu-His-Asp-Ile (SEQ ID NO:34), Leu-Glu-His-Asp-Ile (SEQ ID NO:35), Val-Glu-Ile-Asp-Ile (SEQ ID NO:36), Val-Glu-His-Asp-Ile (SEQ ID NO:37), Ile-Glu-Thr-Asp-Ile (SEQ ID NO:38), Leu-Glu-Thr-Asp-Ile (SEQ ID NO:39), Ile-Glu-Ala-Asp-Ile (SEQ ID NO:40), Asp-Asp-Asp-Asp-Lys (SEQ ID NO:41), Arg-Gly-Glu-Ile (SEQ ID NO:42), Arg-Gly-Asp-Ile (SEQ ID NO:43), Arg-Gly-Asp-Ile (SEQ ID NO:44), Arg-Gly-Asp-Ala (SEQ ID NO:45), Ile-Glu-Pro-Asp-Ile (SEQ ID NO:46), Glu-Asn-Leu-Tyr-Phe-Gln-Gly (SEQ ID NO:3), Glu-Asn-Leu-Tyr-Phe-Gln-Ser (SEQ ID NO:5), and any other proteolytic sites known in this field.

The His-tag is preferably composed of three to eight histidine residues.

In one embodiment of the invention, a fusion protein comprises the fusion carrier protein as defined above, linked to at least one target peptide. The target peptide can be linked to the C- or N-terminus of the fusion carrier protein. Typically, the target peptide has a sequence between 10 and 200 amino acids in length.

In one embodiment of the invention, the DNA sequence of a fusion protein is codon-optimized for efficient translation in its cellular host.

In one embodiment of the invention, the target peptide is preferably selected from the group of peptide consisting of corticorelin, PTH, GLP-1 and its analogs exenatide and liragultide, enfuvirtide, calcitonin, bivalirudin, ziconotide, sermorelin, somatorelin, secretin, teduglutide, and proinsulin, hirudin, growth hormone, growth factors, growth hormone releasing factors, corticotropin, release factor, deslorelin, desmopressin, elcatonin, glucagons, leuprolide, leuteinizing hormone-releasing hormone, secretin, somatisation, thyrotropin-releasing hormone, triptorelin, vasoactive intestinal peptide, interferons, parathyroid hormone, BH3 peptides, beta-amyloidosis peptide or fragments thereof.

The fusion protein preferably further comprises a peptidic cleavage site between the fusion carrier protein and the target peptide.

In accordance with the present invention, there is further provided a nucleic acid sequence encoding the fusion protein described above. This nucleic acid sequence is codon-optimized for efficient translation in its cellular host.

Still in accordance with the present invention, there is provided an expression vector comprising the nucleic acid sequence described above, operably linked to a promoter for expression of said nucleic acid sequence coding for the fusion protein. The promoter can be for example the pL promoter, λ, promoter, pBAD promoter, trc promoter, or T7 promoter.

Further in accordance with the present invention, there is provided a host cell, such as *E. coli* Top10, DH5α, DH10b, BL21, or JM101, transformed with the expression vector described above. Preferably, the host cell is from *E. coli* or *B. subtilis*. Alternatively, the host cell can be a yeast cell, an insect cell, or a mammalian cell.

In accordance with the present invention, there is provided a method for producing a fusion protein comprising the step of culturing the host cell as defined above under suitable conditions for expression of the expression vector, thereby producing a fusion protein. The suitable conditions can comprise an inducer for inducing the host cell to express the expression vector. Such inducer can be arabinose, IPTG or temperature. In one embodiment of the invention, the method further comprises a step of purification of the fusion protein produced.

The step of purification preferably comprises at least one of alcohol precipitation, ion exchange, and affinity purification using Ni-NTA agarose resin. In such method, the fusion protein is preferably further subjected to a proteolytic digestion to release the target peptide from the fusion protein. The proteolytic digestion can be for example achieved by CNBr, formic acid or HCl or by thrombin, or a protease, such as trypsin. The target peptide released can be further purified by HPLC.

In accordance with the present invention, there is provided the use of either a fusion carrier protein, or a nucleic acid, both as defined above, for expressing a target peptide. The nucleic acid can be used in an expression vector for expressing the target protein. A host cell as described above can also be used for expressing a target protein.

For the purpose of the present invention the following terms are defined below.

The term "sfGFP" or "superfolder green fluorescent protein" as used herein refers to a polypeptide derived from or based on the protein sequences of superfolder green fluorescent protein and its mutants (Pedelacq J. D. et al., Nature Biotechnology, 1; 79-88, 2006; and Tansila N. et al., Biotechnology Letters, 30; 1391-1396, 2008) and other permuted, truncated mutants, or hybrid forms in which certain amino acids have been deleted or replaced and modifications such as where one or more amino acids have been changed to a modified amino acid or unusual amino acid and modifications such as glycosylation so long as the hybrid or modified form retains the biological activity of sfGFP as a carrier protein. Preferred variants are those that have conservative amino acid substitutions made at one or more predicted non essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta branched side chains (e.g., threonine, valine, isoleucine) and aromatic side chains (e.g., tyrosine, phenylalanine, tryptophan, histidine). Thus, a predicted nonessential amino acid residue in a sfGFP is replaced with another amino acid residue from the same side chain family. Alternatively, in another embodiment, mutations can be introduced randomly along all or part of a sfGFP coding sequence, such as by saturation mutagenesis, and the resultant mutants can be screened to identify mutants that retain activity.

The amino acid sequence of the entire super folder green fluorescent protein without the first methionine and a code-optimized nucleic acid sequence of DNA encoding the protein are presented as SEQ ID NO:1 and SEQ ID NO:2 respectively.

The target peptide refers to any small protein or oligopeptide desired as a product. For practical applications of the invention, a peptide should contain at least ten amino acid residues linked by peptide bonds or at most two hundred amino acid residues linked by peptide bonds.

The "cleavage site" as used herein refers to the amino acid sequence, which contains an amino acid or a sequence of amino acids that provides a recognition site for a chemical agent or an enzyme such that the peptide chain is cleaved at that site by the chemical agent or enzyme.

A "transformed host cell" refers to a bacterial, yeast, insect, or mammalian cell that contains recombinant material or a bacterial, yeast, insect, or mammalian cell that contains genetic material required for the expression of a recombinant product. The genetic material many be introduced into the cell by any known method including transformation, transduction, electroporation and infection. Generally, throughout the present application, the term "transformed" or "transformation" will be used to refer to indistinctly to any of the known method referred above.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF EXEMPLARY EMBODIMENTS

Figure 1A:
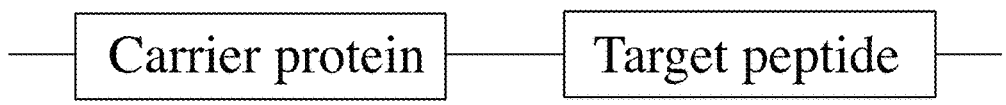
FIG. 1A and FIG. 1B illustrate possible arrangement of the fusion protein of the present invention, wherein, a target peptide is linked to the C-terminus (FIG. 1A) or the N-terminus (FIG. 1B) or the carrier protein.

The expression of recombinant peptides by fusion proteins in either soluble form or in inclusion bodies is a well-known methodology. The present invention utilizes a novel carrier protein to provide an alternative approach for the production of recombinant peptides. The carrier protein is derived from superfolder green fluorescent protein. Recombinant peptides encoded by and released from fusion proteins are recovered according to these methods described herein. The invention provides fusion protein constructs to establish a new, low cost and highly efficient method for large-scale preparation of recombinant peptides.

In accordance with the present invention, there is thus provided a method for the production of recombinant peptides by use of a novel fusion protein. The carrier protein is superfolder green fluorescent protein or one of its mutants. The fusion protein led by superfolder green fluorescent protein is highly expressed in *E. coli*. The superfolder green florescent protein and the target peptide may be linked through a proteolytically sensitive (cleavage) site. The cleavage site is typically a specific amino acid or a specific sequence of amino acids to generate fusion proteins, which are selectively cleaved by a cleavage agent. The cleavage agent can be a chemical agent such as cyanogen bromide or acid. The cleavage agent can also be an endopeptidase such as trypsin, thrombin, enterokinase, or another specific protease.

One embodiment of the invention provides an improved method for obtaining a recombinant peptide from bacterial cells after expression inside the cells of a fusion protein in insoluble inclusion bodies. Expression of the fusion protein as inclusion bodies increases the production yield of the recombinant peptide and protects the integrity of the target peptide.

The second embodiment of the invention is directed to an improved method to simplify purification steps by the insertion of one or more His-tag into superfolder green fluorescent protein. After cleavage of the fusion protein is achieved by a chemical reagent or by an endopeptidase, the superfolder green fluorescent protein tag can be removed by repeating the His-tag affinity purification. Thus, the contaminations from digestion of other cellular proteins can be generally reduced.

The third embodiment is directed to a method to express the fusion proteins in which methionine residues link the target peptides and the carrier superfolder green florescent protein. The fusion protein is expressed in inclusion bodies and purified under a denaturing condition, e.g. with urea or guanidinium chloride. The fusion protein can be solubilized in formic acid and then cleaved with cyanogen bromide to release the target peptide. After the cleavage of the fusion protein, the fragment containing superfolder green fluorescent protein can be removed by chromatography.

The fourth embodiment is directed to a method to express the target peptides containing methionine residues. The fusion protein is expressed in inclusion bodies and purified under a denaturing condition, e.g. with urea or guanidinium chloride. The fusion protein can be refolded by dialysis against a physiological buffer. The fusion protein can be then cleaved with a proteolytic enzyme such as trypsin, TEV protease or thrombin to release the target peptide. After the cleavage of the fusion protein, the fragment containing superfolder green fluorescent protein can be removed by chromatography.

Figure 1B:

The fifth embodiment of this invention covers the fusion of the target peptide to the C- or N-terminus of the carrier protein that is superfolder green fluorescent protein as illustrated in FIG. 1A & FIG. 1B. The size of the target peptide can be from ten to two hundred amino acid residues. The carrier protein has the amino acid sequence listed in SEQ ID NO:1.

Figure 2A:
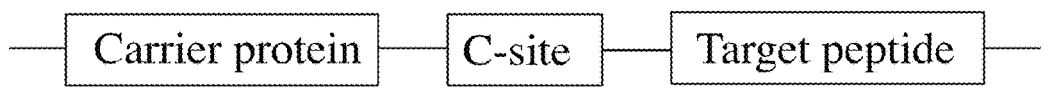
FIG. 2A and FIG. 2B illustrate various embodiments of the fusion protein of FIG. 1A and FIG. 1B, wherein a cleavage site (C-site) links the carrier protein and the target peptide.
Figure 2B:
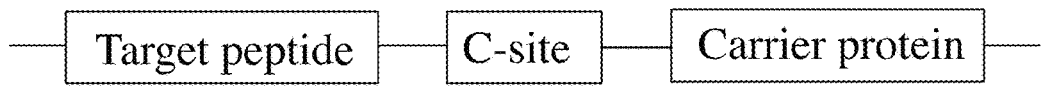

The size of the fusion protein will vary depending on the nature and number of copies of the target peptide. The fusion protein should be large enough to avoid degradation by endogenous proteases. The fusion protein can be arranged in two ways as illustrated in FIG. 1A and FIG. 1B. Alternatively, the target peptide is linked either to the N-terminus or to the C-terminus of the carrier protein (superfolder green fluorescent protein) via a cleavage site of a specific amino acid sequence (FIG. 2A and FIG. 2B). In FIG. 2A and FIG. 2B, C-site contains an amino acid or a sequence of amino acids that provides a recognition site for a chemical or enzymatic reaction such that the a chemical agent or an enzyme cleaves the peptide chain at that site.

Figure 3A:
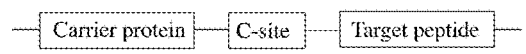
FIG. 3A and FIG. 3B illustrate two other embodiments of the fusion protein of the present invention with single (FIG. 3A) and multiple (FIG. 3B) repeats of target peptides.
Figure 3B:
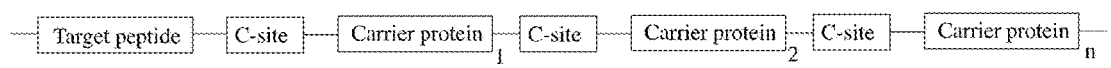
Figure 4A:
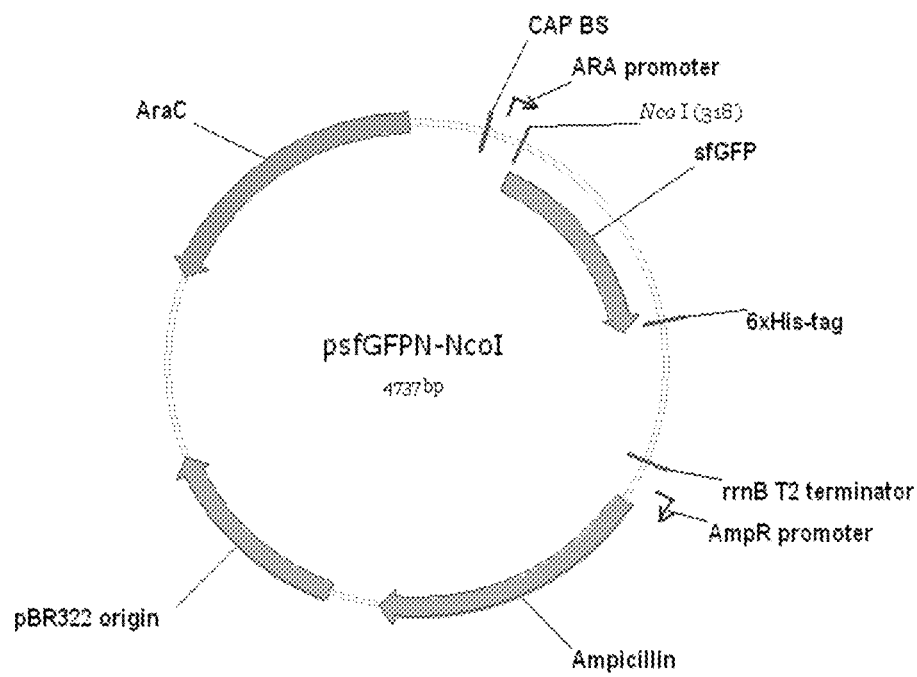
FIG. 4A and FIG. 4B illustrate respectively two plasmids pSFGFPN-NcoI and pSFGFPC-MCS expression vectors containing superfolder green fluorescent protein used as the carrier protein.
Figure 4B:
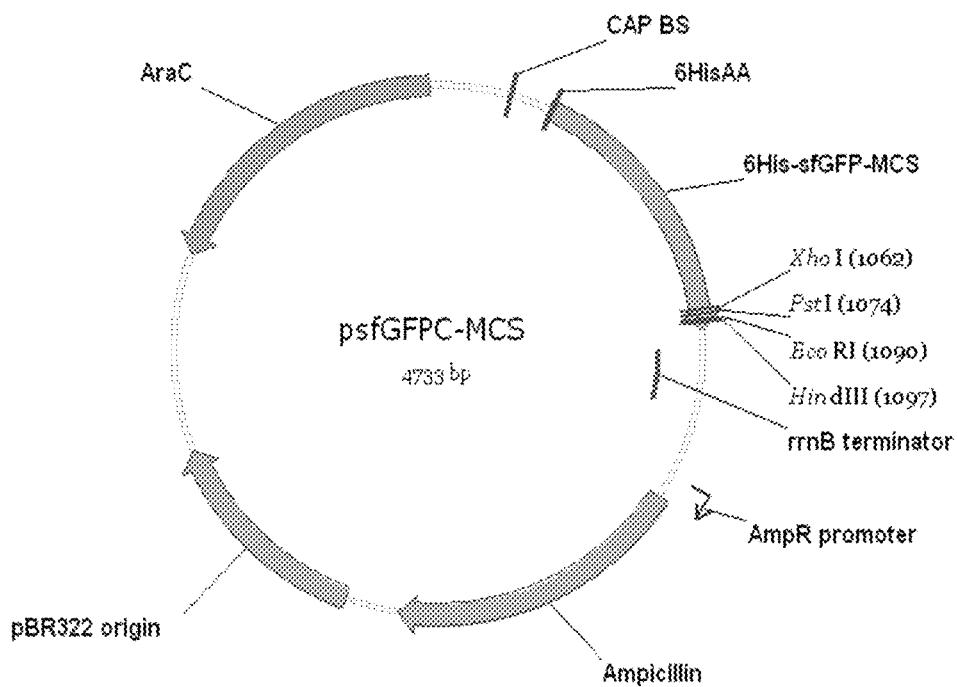

The target peptide can be composed of one or more consecutive sequences of ten to two hundred amino acid residues. The large peptides are in particular those derived from protein sequences that do not have uniquely folded three dimentional structures. The various target peptides can have several forms as shown in FIG. 3A and FIG. 3B. In FIG. 3A, one includes a single copy of the target peptide. In FIG. 3B, a second is composed of multiple tandem repeats of a single target peptide. Each repeat may be the same or a different peptide. The repeats are linked by an "interconnecting" sequence, which may be Met, Lys, Arg, Glu-Asn-Leu-Tyr-Phe-Gln-Gly (SEQ ID NO:3), Glu-Asn-Leu-Tyr-Phe-Gln-Ser (SEQ ID NO:5), or other suitable amino acid sequences. The interconnecting sequence is not necessarily different the "connecting sequence" which links the carrier protein and the target peptide. The use of different connection linkers provide an advantage that two or more different cleavage agents (e.g. chemicals or enzymes) can individually release the target peptide from the fusion protein and separate the individual target peptides from each other.

Particular embodiments of the fused peptides which may appear as single or multiple-linked repeats include corticorelin, PTH, GLP-1 and its analogs exenatide and liragultide, enfuvirtide, calcitonin, bivalirudin, ziconotide, sermorelin, somatorelin, secretin, teduglutide, and proinsulin, hirudin, growth hormone, growth factors, growth hormone releasing factors, corticotropin, release factor, deslorelin, desmopressin, elcatonin, glucagons, leuprolide, leuteinizing hormone-releasing hormone, secretin, somatisation, thyrotropin-releasing hormone, triptorelin, vasoactive intestinal peptide, interferons, parathyroid hormone, BH3 peptides, beta-amyloidosis peptide. One common property of these peptides is than they all have flexible and fragile conformations that make them unstable and prone to proteolytic degradation.

The cleavage site and the target peptide are preferably selected so that the target peptide does not contain the same cleavage site. The cleavage sites include Met, Lys, Arg, Glu-Asn-Leu-Tyr-Phe-Gln-Gly (SEQ ID NO:3), Glu-Asn-Leu-Tyr-Phe-Gln-Ser (SEQ ID NO:5), or other suitable amino acid sequences. New cleavage sites may be designed in order to use a chemical cleavage reagent or an enzyme or the combination of the two. In some instances, it may be desirable to utilize a cleavage site to introduce a specific functional group to the C-terminus of the target peptide such as cleavage by cyanogen bromide.

The DNA sequence encoding the target peptide may be obtained from natural sources (e.g. genomic DNA) or via chemical synthesis utilizing the codon preference of bacterial cells or other host cells.

One embodiment of the invention provides a method to amplify the DNA sequence encoding a particular peptide contained in genomic DNA. Typically, two primers are designed to introduce two unique restriction sites at each end of the PCR product. The PCR reaction is performed in a PCR amplification device that provides control of the reaction temperature. A PCR DNA polymerase, e.g. the Taq, Pfu, Phusion DNA polymerase, is used in a PCR reaction and the reaction condition follows the protocol provided by the suppliers. PCR products are subjected to the direct digestion with at least one restriction enzyme or if necessary a cleanup procedure is conducted prior to restriction enzyme digestion. The digestion reaction mixture is cleaned up by DNA purification methods. DNA purification can be achieved by use of agarose gel electrophoresis or a PCR purification kit. The purified PCR products are used as inserts encoding target peptides. In some instances, the insert encoding the target peptide is not available from a natural source. In this latter case, the DNA fragment encoding the target peptide is prepared through chemical synthesis. Generally, at least two oligonucleotide primers are chemically synthesized with at least one restriction enzyme site at either end. The two oligonucleotides may be complementary or overlapped in the middle region with at lest ten base pairs. The PCR amplification may be employed to generate an intact insert from overlapped oligonucleotides.

The DNA sequence encoding a fusion protein contains at least four parts including a DNA sequence of the affinity tag, a DNA sequence of the carrier protein-superfolder green fluorescent protein, a DNA sequence of the cleavage site and a DNA sequence of the target peptide. Typically the arrangement of DNA sequence segments can be the same as those described in FIG. 2A and FIG. 2B. The DNA sequence of the affinity tag may be inserted in any place in the DNA sequence of the fusion protein. The DNA sequence of the fusion protein is ligated into any bacterial expression plasmid to construct an expression vector. The expression vector contains at least one promoter e.g. lac, T7, Tac, lamda, pL, or pBAD and one antibiotic marker, e.g. ampicillin, kanamycin, or tetracycline.

The constructed expression vector may be transformed into a bacterial host cell to replicate plasmid for small-scale DNA preparation (mini-prep) and sequencing. The identity of the construct is confirmed by DNA sequencing and the expression vector is transformed into a bacterial host cell to express the fusion protein. The cells harboring the fusion protein expression vector may be cultured in the LB medium or a minimal medium in the presence of at least one antibiotic. The expression of the fusion protein is induced with an inducer, eg. IPTG, galactoside, nalidixic acid, temperature, or arabinose.

The purification of fusion protein refers to the procedure by which the fusion protein is isolated from host cells. Cells are typically collected by centrifugation or filtration. The cell pellet is typically resuspended in the lysis buffer which contains 50 mM phosphate, 10 mM Tris, and 50 mM NaCl. The lysis buffer may contain a chaotropic agent, e.g. urea or guanidinium chloride. Suspended cells may be further subjected to French Press or ultra-sonication to thoroughly break the cells. The lysate is subjected to centrifugation to isolate the desired fusion protein from others. In some instances, the fusion protein is isolated from cells as pure inclusion bodies. The inclusion bodies may be isolated from a crude cell lysate by conventional techniques, e.g. by centrifugation. The crude inclusion bodies may be subjected to an initial purification step such as washing by a solution of 50 mM phosphate, 1 mM EDTA, pH 7.5 once and then washing with the same buffer containing low concentration of chaotropic reagent such as urea or guanidinium chloride at least twice. Pure inclusion bodies will be dissolved in a chaotropic buffer and then is subjected to refolding. The refolding process may be carried out by dialysis of the suspended sample against a physiological buffer or by removal of salts through a reverse-phase chromatographic column and followed by freeze-drying. In some instances, the fusion protein is produced in insoluble inclusion bodies inside cells but no affinity tag was engineered. In this case, the fusion protein in the lysate is roughly purified by solvent extraction and further purified by ion-exchange chromatography. If necessary, the fusion protein may be purified by reverse-phase HPLC. In other instances, the fusion protein may be purified through affinity chromatography such as His-tag binding Ni-NTA affinity beads under either native condition or denaturing conditions.

After cleavage, the mixture is used to isolate the target peptide from the carrier protein. In some instances, the mixture may be used directly for HPLC purification. The pH value of the mixture should be adjusted to below 3.0 and the sample is filtered to remove particles prior to HPLC purification. In some instances, the mixture is diluted with water (e.g. to ~10 fold) and lyophilized to dryness and then purified by reverse-phase HPLC column using an acetonitrile-water gradient containing 0.1% TFA. In other instances, the mixture is initially purified by His-tag affinity chromatography and reverse-phase chromatography to remove salts, the carrier protein, undigested fusion protein and non-specifically digested peptides. Finally, the pure peptide is lyophilized and the identity is confirmed by mass spectrometry.

Table 1 lists some recombinant peptides exemplified herein below, which has been expressed with the current invention. The data show that the present expression systems can efficiently produce pure peptides in high-yield.

TABLE 1

Examples of the expressed recombinant peptides

| Peptide | Size (AA) | Yield (mg/L) |
| --- | --- | --- |
| Proinlusin lispro | 82 | >300 |
| proinsulin | 82 | >300 |
| Proinsulin glargine | 82 | >300 |
| PTH | 34 | >50 |
| calcitonin | 33 | >50 |
| GLP-1 | 39 | >50 |

The term "isolated" or "purified" material refers to material that is substantially or essentially free from components that normally accompany it as found in its native state. For instance, this refers to the DNA segment as originally isolated, and does not exclude other isolated proteins, genes, or coding regions later added to the composition by the hand of man. Purity and homogeneity are typically determined using analytical chemistry techniques such as polyacrylamide gel electrophoresis or high performance liquid chromatography. A protein that is the predominant species present in a preparation is substantially purified. An isolated nucleic acid is separated from other open reading frames that flank the gene and encode proteins other than the gene.

As used herein, an "isolated" or "purified" protein or biologically active portion thereof is substantially free of cellular material or other contaminating proteins from the cell or tissue source from which the fusion protein or target protein is derived, or substantially free from chemical precursors or other chemicals when chemically synthesized. The language "substantially free of cellular material" includes preparations of fusion protein or target protein in which the protein is separated from cellular components of the cells from which it is isolated or recombinantly produced. In one embodiment, the language "substantially free of cellular material" includes preparations of target protein having less than about 30% (by dry weight) of non-target protein (also referred to herein as a "contaminating protein"), more preferably less than about 20% of non-target protein, still more preferably less than about 10% of non-target protein, and most preferably less than about 5% non-target protein. When the target protein or biologically active portion thereof is recombinantly produced, it is also preferably substantially free of culture medium, i.e., culture medium represents less than about 20%, more preferably less than about 10%, and most preferably less than about 5% of the volume of the protein preparation. In embodiments, the purity of target protein is at least 80%, at least 90%, at least 95%, or at least 98%.

The present invention additionally relates to nucleic acids that encode the fusion protein of the invention. Nucleic acids encoding the fusion proteins may be obtained by any method known in the art (e.g., by PCR amplification using synthetic primers hybridizable to the 3' and 5' termini of the sequence and/or by cloning from a cDNA or genomic library using an oligonucleotide sequence specific for the given gene sequence).

For recombinant expression of the target protein, the nucleic acid containing all or a portion of the nucleotide sequence encoding the protein may be inserted into an appropriate expression vector (i.e., a vector that contains the necessary elements for the transcription and translation of the inserted peptide coding sequence). In some embodiments, the regulatory elements are heterologous (i.e., not the native gene promoter). Alternately, the necessary transcriptional and translational signals may also be supplied by the native promoter for the genes and/or their flanking regions.

A variety of host vector systems may be utilized to express the peptide coding sequence(s). These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host vector system utilized, any one of a number of suitable transcription and translation elements may be used.

Promoter/enhancer sequences within expression vectors may utilize plant, animal, insect, or fungus regulatory sequences, as provided in the invention. For example, promoter/enhancer elements can be used from yeast and other fungi (e.g., the GAL4 promoter, the alcohol dehydrogenase promoter, the phosphoglycerol kinase promoter, the alkaline phosphatase promoter). Alternatively, or in addition, they may include animal transcriptional control regions, e.g., (i) the insulin gene control region active within pancreatic β cells (see, e.g., Hanahan, et al., 1985. Nature 315: 115 122); (ii) the immunoglobulin gene control region active within lymphoid cells (see, e.g., Grosschedl, et al., 1984. Cell 38: 647 658); (iii) the albumin gene control region active within liver (see, e.g., Pinckert, et al., 1987. Genes and Dev 1: 268 276; (iv) the myelin basic protein gene control region active within brain oligodendrocyte cells (see, e.g., Readhead, et al., 1987. Cell 48: 703 712); and (v) the gonadotropin releasing hormone gene control region active within the hypothalamus (see, e.g., Mason, et al., 1986. Science 234: 1372 1378), and the like.

Expression vectors or their derivatives include, e.g. human or animal viruses (e.g., vaccinia virus or adenovirus); insect viruses (e.g., baculovirus); yeast vectors; bacteriophage vectors (e.g., lambda phage); plasmid vectors and cosmid vectors.

A host cell strain may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically engineered peptides. Moreover, different host cells possess characteristic and specific mechanisms for the translational and post translational processing and modification (e.g., glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an unglycosylated core peptide; whereas expression within mammalian cells ensures "native" glycosylation of a heterologous peptide.

As described above, also included in the invention are derivatives, fragments, homologs, analogs and variants of sfGFP for use as a carrier protein and nucleic acids encoding these proteins or polypeptides. For nucleic acids, derivatives, fragments, and analogs provided herein are defined as sequences of at least 6 (contiguous) nucleic acids, and which have a length sufficient to allow for specific hybridization. For amino acids, derivatives, fragments, and analogs provided herein are defined as sequences of at least 4 (contiguous) amino acids, a length sufficient to allow for specific recognition of an epitope.

The length of the fragments is less than the length of the corresponding full-length nucleic acid or polypeptide from which sfGFP, or nucleic acid encoding same, is derived. Derivatives and analogs may be full length or other than full length, if the derivative or analog contains a modified nucleic acid or amino acid. Derivatives or analogs of sfGFP include, e.g., molecules including regions that are substantially homologous to the protein, in various embodiments, by at least about 30%, 50%, 70%, 80%, or 95%, 98%, or even 99%, identity over an amino acid sequence of identical size or when compared to an aligned sequence in which the alignment is done by a computer homology program known in the art. For example sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

In the case of polypeptide sequences, which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Thus, included in the invention are peptides having mutated sequences such that they remain homologous, e.g. in sequence, in function, and in antigenic character or other function, with a protein having the corresponding parent sequence. Such mutations can, for example, be mutations involving conservative amino acid changes, e.g., changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Of course, other polypeptides will meet the same criteria.

In embodiments, the carrier protein of the invention has a sequence at least 80% (e.g., at least 85%, at least 90%, at least 95%, or at least 97%) identical to SEQ ID NO: 1. In embodiments, the fusion protein of the invention includes a target protein and a carrier protein that has a sequence at least 80% (e.g., at least 85%, at least 90%, at least 95%, or at least 97%) identical to SEQ ID NO: 1. In embodiments, the nucleic acid encoding the fusion protein includes a The invention also encompasses allelic variants of the disclosed polynucleotides or peptides; that is, naturally occurring alternative forms of the isolated polynucleotide that also encode peptides that are identical, homologous or related to that encoded by the polynucleotides. Alternatively, non naturally occurring variants may be produced by mutagenesis techniques or by direct synthesis.

Species homologs of the disclosed polynucleotides and peptides are also provided by the present invention. "Variant" refers to a polynucleotide or polypeptide differing from the polynucleotide or polypeptide of the present invention, but retaining essential properties thereof. Generally, variants are overall closely similar, and in many regions, identical to the polynucleotide or polypeptide of the present invention. The variants may contain alterations in the coding regions, non coding regions, or both.

In some embodiments, altered sequences include insertions such that the overall amino acid sequence is lengthened while the protein retains trafficking properties. Additionally, altered sequences may include random or designed internal deletions that shorten the overall amino acid sequence while the protein retains transport properties.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1. Construction of Expression Vector pSFGFPN-NcoI

The construction of all plasmids in this invention followed standard cloning and QuikChange site-directed mutagenesis procedures using Phusion high-fidelity DNA polymerase from New England Biolabs Inc. Sequences of all plasmids constructed were verified by DNA sequencing. All oligonucleotide primers were purchased from Integrated DNA Technologies, Inc.

The plasmid pSFGFPN-NcoI contained a codon-optimized gene coding superfolder green fluorescent protein with a C-terminal 6×His-tag. There was also a NcoI restriction site that overlapped the first two amino acid coding nucleotides of the superfolder green fluorescent protein gene. This site was generated for the future cloning of a target peptide gene into the plasmid to form a fusion gene with superfolder green fluorescent protein at its C-terminus. To construct pSFGFPN-NcoI, two oligonucleotide primers 5'-AATTAACCATGGTTAGCAAAGGTG-3' (SEQ ID NO:47) and 5'-GATCTCGAGCTTTAATGGTGATGATGATGGTGGCTGCCTTTATACAG-3' (SEQ ID NO:48) were used to amplify a synthetic superfolder green fluorescent protein DNA using polymerase chain reactions (PCRs). The first primer contains a NcoI restriction site; the second primer contains a XhoI restriction site. The superfolder green fluorescent protein DNA shown as SEQ ID NO:2 was synthesized in Epoch biolabs Inc and codon optimized for efficient translation of the coded superfolder green fluorescent protein in *E. coli*. The PCR-amplified DNA was digested with NcoI and XhoI restriction enzymes for three hours. The finally digested DNA was separated by agarose electrophoresis. The desired band for the digested DNA was cut and extracted using Qiagen gel extraction kits. The extracted digested DNA was then ligated with a precut pBAD/Myc-His A vector from Invitrogen Inc using T4 DNA ligase. The precut pBAD/Myc-His A vector was obtained by digesting pBAD/Myc-His A with NcoI and XhoI restriction enzymes and cleaned using Qiagen PCR clean kits. The ligated product was then chemically transformed into Top10 cells. The transformed cells were grown on a lysogeny broth (LB) plate containing 100 µg/mL ampicillin overnight. Five survived colonies were selected to grow in 5 mL liquid LB media for plasmid extraction using Qiagen gel extraction kits. The extracted plasmids were then sequenced using two sequencing oligonucleotide primers 5'-CCTACCTGACGCTTTTTATCGCAACTC-3' (SEQ ID NO:49) and 5'-GGCTGAAAATCTTCTCTCATCCGCC-3' (SEQ ID NO:50) to confirm the correct insert. The finally obtained plasmid is named as pSFGFPN-NcoI.

Example 2: Construction of Expression Vector pSFGFPC-MCS

The plasmid pSFGFPC-MCS contained a codon-optimized gene coding superfolder green fluorescent protein with a N-terminal 6×His-tag. There was also a multiple cloning site (MCS) containing restriction sites for XhoI, BglII, PstI, KpnI, EcoRI and HindIII at the C-terminal end of the superfolder green fluorescent protein gene. This multiple cloning site was generated for the future cloning of a target peptide gene into the plasmid to form a fusion gene with superfolder green fluorescent protein at its N-terminus. To obtain pSFGFPC-MCS, two primers 5'-AACCATGGTTCACCATCATCATCACCATGCGGCGAGCAA-3' (SEQ ID NO:51) and 5'-ATCTCGAGCTTTATACAGTTCATCCATA-3' (SEQ ID NO:52) were used to amplify the same synthetic superfolder green fluorescent protein DNA using PCR. The first primer contains a NcoI restriction site; the second primer contains a XhoI restriction site. The PCR-amplified DNA was digested with NcoI and XhoI restriction enzymes for three hours. The finally digested DNA was separated by agarose electrophoresis. The desired band for the digested DNA was cut and extracted using Qiagen gel extraction kits. The extracted digested DNA was then ligated with a precut pBAD/Myc-His A vector from Invitrogen Inc using T4 DNA ligase. The precut pBAD/Myc-His A vector was obtained by digesting pBAD/Myc-His A with NcoI and XhoI restriction enzymes and cleaned using Qiagen PCR clean kits. The ligated product was then chemically transformed into Top10 cells. The transformed cells were grown on a LB plate containing 100 µg/mL ampicillin overnight. Five survived colonies were selected to grow in 5 mL liquid LB media for plasmid extraction using Qiagen gel extraction kits. The extracted plasmids were then sequenced using two sequencing oligonucleotide primers 5'-CCTACCTGACGCTTTTTATCGCAACTC-3' (SEQ ID NO:53) and 5'-GGCTGAAAATCTTCTCTCATCCGCC-3' (SEQ ID NO:54) to confirm the correct insert. The finally obtained plasmid is named as pSFGFPC-MCS.

Example 3: Construction of Expression Vector pSFGFPN-Prolispro

The expression vector pSFGFPN-prolispro contained a gene coding the precursor protein (prolispro; its amino acid sequence is shown as SEQ ID NO:7) of human insulin analog lispro fused at the N-terminus of superfolder green fluorescent protein that also has a C-terminal 6×His tag. In front of the prolispro gene, a tripeptide Met-Ala-Arg coding sequence was inserted for the following easy cleavage of this tripetitide with trypsin. The linker peptide between prolispro and superfolder green fluorescent protein was an octapeptide Arg-Glu-Asn-Leu-Tyr-Phe-Gln-Gly. This octapeptide can be hydrolyzed by both trypsin after Arg and TEV protease between Gln and Gly. The DNA sequence for this octapeptide is also codon optimized for efficient translation in *E. coli*. To construct pSFGFPN-prolispro, two primers 5'-GAATTAACCATGGCGCGTTTCGTTAAC-CAACACCTG-3' (SEQ ID NO:55) and 5'-AACCCATG-GCTCCCTGAAAATACAGGTTTTCACGATTACAG-TAATTTTC-3' (SEQ ID NO:56) were used to amplify a synthetic prolispro DNA using PCR. Both primers contain a NcoI restriction site. The synthetic prolispro DNA was provided by Epoch Biolab Inc. and its sequence shown as SEQ ID NO: 8 was optimized for efficient translation in *E. coli*. The PCR-amplified DNA was digested with NcoI restriction enzyme for three hours. The finally digested DNA was separated by agarose electrophoresis. The desired band for the digested DNA was cut and extracted using Qiagen gel extraction kits. The extracted digested DNA was then ligated with a precut psfGFPN-NcoI vector using T4 DNA ligase. The precut psfGFPN-NcoI vector was obtained by digesting psfGFPN-NcoI with NcoI and DpnI restriction enzymes for three hours and cleaned using Qiagen PCR clean kits. The ligated product was then chemically transformed into Top10 cells. The transformed cells were grown on a LB plate containing 100 μg/mL ampicillin overnight. Five survived colonies were selected to grow in 5 mL liquid LB media for plasmid extraction using Qiagen gel extraction kits. The extracted plasmids were then sequenced using a sequencing oligonucleotide primer 5'-CCTACCTGACGCTTTT-TATCGCAACTC-3' (SEQ ID NO:57) to confirm the correct insert. The finally obtained plasmid is named as pSFGFPN-prolispro. In this plasmid, the fusion gene codes a fusion protein with a sequence shown as SEQ ID NO:9 and has a DNA sequence as SEQ ID NO:10.

Example 4: Construction of Expression Vector pSFGFPN-Proinsulin

The expression vector pSFGFPN-proinsulin contained a gene coding the precursor protein (proinsulin; its amino acid sequence is shown as SEQ ID NO:11 and its nucleotide sequence is shown as SEQ ID NO:12) of human insulin fused at the N-terminus of superfolder green fluorescent protein that also has a C-terminal 6×His tag. In front of the proinsulin gene, a tripeptide Met-Ala-Arg coding sequence was inserted for the following easy cleavage of this tripeptitide with trypsin. The linker peptide between proinsulin and superfolder green fluorescent protein was an octapeptide Arg-Glu-Asn-Leu-Tyr-Phe-Gln-Gly. This octapeptide can be hydrolyzed by both trypsin after Arg and TEV protease between Gln and Gly. The DNA sequence for this octapeptide is also codon optimized for efficient translation in *E. coli*. To construct pSFGFPN-proinsulin, two primers 5'-CCGAAAACTCGTCGCGAAGCAGAGG-3' (SEQ ID NO:58) and 5'-AGTATAGAAGAAGCCACGTTCACC-3' (SEQ ID NO:59) were used to amplify the expression vector pSFGFPN-prolispro using PCR. The PCR-amplified DNA was phosphorylated using T4 polynucleotide kinase and then digested by DpnI restriction enzyme to remove the original pSFGFPN-prolispro. The finally digested DNA was separated by agarose electrophoresis. The desired band was cut and extracted using Qiagen gel extraction kits. The extracted DNA was then ligated to itself using T4 DNA ligase. The ligated product was then chemically transformed into Top10 cells. The transformed cells were grown on a LB plate containing 100 μg/mL ampicillin overnight. Five survived colonies were selected to grow in 5 mL liquid LB media for plasmid extraction using Qiagen gel extraction kits. The extracted plasmids were then sequenced using a sequencing oligonucleotide primer 5'-CCTACCT-GACGCTTTTTATCGCAACTC-3' (SEQ ID NO:60) to confirm the correct insert. The finally obtained plasmid is named as pSFGFPN-proinsulin. In this plasmid, the fusion gene codes a fusion protein with a sequence shown as SEQ ID NO:13 and has a DNA sequence as SEQ ID NO:14.

Example 5: Construction of Expression Vector pSFGFP-Proglargine

The expression vector pSFGFPN-proglargine contained a gene coding the precursor protein (proglargine; its amino acid sequence is shown as SEQ ID NO:15 and its nucleotide sequence is shown as SEQ ID NO:16) of human insulin analog glargine fused at the N-terminus of superfolder green fluorescent protein that also has a C-terminal 6×His tag. In front of the proinsulin gene, a tripeptide Met-Ala-Arg coding sequence was inserted for the following easy cleavage of this tripeptitide with trypsin. The linker peptide between proglargine and superfolder green fluorescent protein was an octapeptide Arg-Glu-Asn-Leu-Tyr-Phe-Gln-Gly. This octapeptide can be hydrolyzed by both trypsin after Arg and TEV protease between Gln and Gly. The DNA sequence for this octapeptide is also codon optimized for efficient translation in *E. coli*. To construct pSFGFPN-proglargine, two primers 5'-CGTGAAAACCTGTATTTTCAGG-3' (SEQ ID NO:61) and 5'-GCCACAGTAATTTTCCAGCTTATAC-3' (SEQ ID NO:62) were used to amplify the expression vector pSFGFPN-proinsulin using PCR. The PCR-amplified DNA was phosphorylated using T4 polynucleotide kinase and then digested by DpnI restriction enzyme to remove the original pSFGFPN-proinsulin. The finally digested DNA was separated by agarose electrophoresis. The desired band was cut and extracted using Qiagen gel extraction kits. The extracted DNA was then ligated to itself using T4 DNA ligase. The ligated product was then chemically transformed into Top10 cells. The transformed cells were grown on a LB plate containing 100 μg/mL ampicillin overnight. Five survived colonies were selected to grow in 5 mL liquid LB media for plasmid extraction using Qiagen gel extraction kits. The extracted plasmids were then sequenced using a sequencing oligonucleotide primer 5'-CCTACCT-GACGCTTTTTATCGCAACTC-3' (SEQ ID NO:63) to confirm the correct insert. The finally obtained plasmid is named as pSFGFPN-proglargine. In this plasmid, the fusion gene codes a fusion protein with a sequence shown as SEQ ID NO:17 and has a DNA sequence as SEQ ID NO:18.

Example 6: Construction of Expression Vector pSFGFPC-PTH

The expression vector pSFGFPC-PTH contained a gene coding PTH (its amino acid sequence is shown as SEQ ID NO:19 and its nucleotide sequence is shown as SEQ ID NO:20) fused at the C-terminus of superfolder green fluorescent protein that also has a N-terminal 6×His tag. The linker peptide between superfolder green fluorescent protein and PTH was a hexapeptide Glu-Asn-Leu-Tyr-Phe-Gln. This hexapeptide can be recognized and hydrolyzed TEV protease after Gln. The DNA sequence for this hexapeptide is also codon optimized for efficient translation in *E. coli*. To construct pSFGFPC-PTH, two primers 5'-ACCTCGAGAT-GAAAACCTGTATTTTCAGTCTGTTTCTGAAA-3' (SEQ ID NO:64) and 5'-TCTAATTCCCTTAGAAGTTGT- TAAGCTCCTG-3' (SEQ ID NO:65) were used to amplify a synthetic PTH gene using PCR. The first primer contains a XhoI restriction site; the second contains a EcoRI restriction site. The synthetic PTH DNA was provided by Epoch Biolabs Inc. and sequence optimized for efficient translation in *E. coli*. The PCR-amplified DNA was digested with XhoI and EcoRI restriction enzymes for three hours. The finally digested DNA was separated by agarose electrophoresis. The desired band for the digested DNA was cut and extracted using Qiagen gel extraction kits. The extracted digested DNA was then ligated with a precut psfGFPC-MCS vector using T4 DNA ligase. The precut psfGFPC-MCS vector was obtained by digesting psfGFPC-MCS with XhoI and EcoRI restriction enzymes for three hours and cleaned using Qiagen PCR clean kits. The ligated product was then chemically transformed into Top10 cells. The transformed cells were grown on a LB plate containing 100 µg/mL ampicillin overnight. Five survived colonies were selected to grow in 5 mL liquid LB media for plasmid extraction using Qiagen gel extraction kits. The extracted plasmids were then sequenced using a sequencing oligonucleotide primer 5'-GGCTGAAAATCTTCTCTCATCCGCC-3' (SEQ ID NO:66) to confirm the correct insert. The finally obtained plasmid is named as pSFGFPC-PTH. In this plasmid, the fusion gene codes a fusion protein with a sequence shown as SEQ ID NO:21 and has a DNA sequence as SEQ ID NO:22.

Example 7: Construction of Expression Vector pSFGFPC-Calcitonin

The expression vector pSFGFPC-PTH contained a gene coding salmon calcitonin (its amino acid sequence is shown as SEQ ID NO:23 and its nucleotide sequence is shown as SEQ ID NO:24) fused at the C-terminus of superfolder green fluorescent protein that also has a N-terminal 6×His tag. The linker peptide between superfolder green fluorescent protein and calcitonin was a hexapeptide Glu-Asn-Leu-Tyr-Phe-Gln. This hexapeptide can be recognized and hydrolyzed TEV protease after Gln. The DNA sequence for this hexapeptide is also codon optimized for efficient translation in *E. coli*. To construct pSFGFPC-calcitonin, two primers 5'-AGCTCGAGATGAAAACCTGTATTTTCAGTGCTCTGCGCTGTC-3' (SEQ ID NO:67) and 5'-TCGAATTCCCTTACGGGGTACCAGA-3' (SEQ ID NO:68) were used to amplify a synthetic calcitonin gene using PCR. The first primer contains a XhoI restriction site; the second contains a EcoRI restriction site. The synthetic calcitonin DNA was provided by Epoch Biolabs Inc. and sequence optimized for efficient translation in *E. coli*. The PCR-amplified DNA was digested with XhoI and EcoRI restriction enzymes for three hours. The finally digested DNA was separated by agarose electrophoresis. The desired band for the digested DNA was cut and extracted using Qiagen gel extraction kits. The extracted digested DNA was then ligated with a precut psfGFPC-MCS vector using T4 DNA ligase. The precut psfGFPC-MCS vector was obtained by digesting psfGFPC-MCS with XhoI and EcoRI restriction enzymes for three hours and cleaned using Qiagen PCR clean kits. The ligated product was then chemically transformed into Top10 cells. The transformed cells were grown on a LB plate containing 100 µg/mL ampicillin overnight. Five survived colonies were selected to grow in 5 mL liquid LB media for plasmid extraction using Qiagen gel extraction kits. The extracted plasmids were then sequenced using a sequencing oligonucleotide primer 5'-GGCTGAAAATCTTCTCTCATCCGCC-3' (SEQ ID NO:69) to confirm the correct insert. The finally obtained plasmid is named as pSFGFPC-calcitonin. In this plasmid, the fusion gene codes a fusion protein with a sequence shown as SEQ ID NO:25 and has a DNA sequence as SEQ ID NO:26.

Example 8: Construction of Expression Vector pSFGFPC-GLP1

The expression vector pSFGFPC-GLP1 contained a gene coding GLP-1 (its amino acid sequence is shown as SEQ ID NO:27 and its nucleotide sequence is shown as SEQ ID NO:28) fused at the C-terminus of superfolder green fluorescent protein that also has a N-terminal 6×His tag. The linker peptide between superfolder green fluorescent protein and GLP-1 was a hexapeptide Glu-Asn-Leu-Tyr-Phe-Gln. This hexapeptide can be recognized and hydrolyzed TEV protease after Gln. The DNA sequence for this hexapeptide is also codon optimized for efficient translation in *E. coli*. To construct pSFGFPC-GLP1, two primers 5'-AGCTCGAGATGAAAACCTGTATTTTCAGCACGGTGGTGGTAC-3' (SEQ ID NO:70) and 5'-TCGAATTCCCTTAAGACGGCGGCGGCGCACC-3' (SEQ ID NO:71) were used to amplify a synthetic GLP-1 gene using PCR. The first primer contains a XhoI restriction site; the second contains a EcoRI restriction site. The synthetic GLP-1 DNA was provided by Epoch Biolabs Inc. and sequence optimized for efficient translation in *E. coli*. The PCR-amplified DNA was digested with XhoI and EcoRI restriction enzymes for three hours. The finally digested DNA was separated by agarose electrophoresis. The desired band for the digested DNA was cut and extracted using Qiagen gel extraction kits. The extracted digested DNA was then ligated with a precut psfGFPC-MCS vector using T4 DNA ligase. The precut psfGFPC-MCS vector was obtained by digesting psfGFPC-MCS with XhoI and EcoRI restriction enzymes for three hours and cleaned using Qiagen PCR clean kits. The ligated product was then chemically transformed into Top10 cells. The transformed cells were grown on a LB plate containing 100 µg/mL ampicillin overnight. Five survived colonies were selected to grow in 5 mL liquid LB media for plasmid extraction using Qiagen gel extraction kits. The extracted plasmids were then sequenced using a sequencing oligonucleotide primer 5'-GGCTGAAAATCTTCTCTCATCCGCC-3' (SEQ ID NO:72) to confirm the correct insert. The finally obtained plasmid is named as pSFGFPC-GLP-1. In this plasmid, the fusion gene codes a fusion protein with a sequence shown as SEQ ID NO:29 and has a DNA sequence as SEQ ID NO:30.

Example 9: Expression of Prolispro

To express the prolispro-sfGFP protein, a sequence confirmed psfGFPN-prolispro plasmid was used to chemically transform *E. coli* Top10 cells. The transformed cells were grown on a LB plate containing 100 µg/mL ampicillin overnight. A single colony was selected to grow in a 5 mL LB culture containing 100 µg/mL ampicillin overnight. This overnight culture was then used to inoculate a 1 L 2YT medium containing µg/mL ampicillin and grown at 37° C. until the $OD_{600}$ was 0.7. A 20% arabinose solution was then added to the medium to final concentration of 0.2% to induce the expression of the fusion protein. The cells were grown for an additional 22 hours and then collected by centrifugation (4500 r.p.m., 20 min, 4° C.). The whole cell culture turned green three hours after induction. The final collected cell pellet showed strong fluorescence even under daylight indicating a very high expression level of the prolispro-sfGFP fusion protein.

Figure 5:
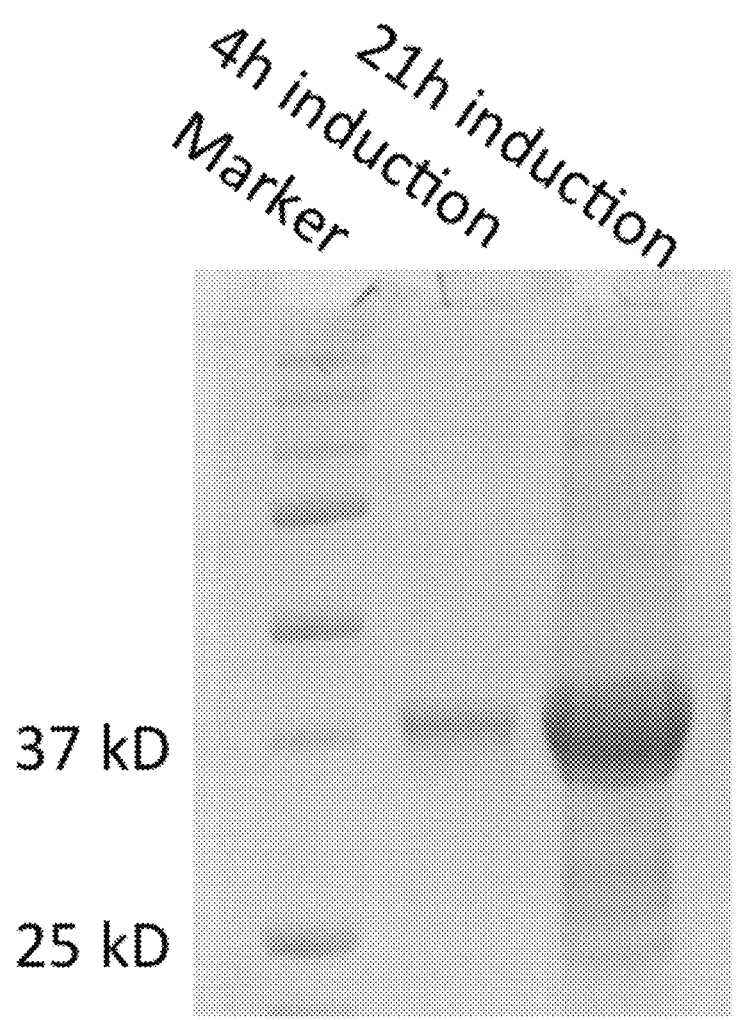
FIG. 5 illustrates a SDS-PAGE of the expressed prolispro-sfGFP fusion protein in the inclusion bodies 4 h and 21 h after induction with arabinose.

The collected cells were re-suspended in 20 mL of lysis buffer (50 mM HEPES, pH 7.4, 500 mM NaCl, 10 mM DTT, 10% glycerol, 0.1% Triton X-100, 5 mM imidazole, and 1 µg/mL lysozyme). The resuspended cells were sonicated and the lysate was clarified by centrifugation (10200 r.p.m., 60 min, 4° C.). The following SDS-PAGE analysis of the supernatant and the cell debris indicating most of the fusion protein was expressed in inclusion bodies as an insoluble form. Therefore, we followed an inclusion body purification protocol to purify the expressed prolispro-sfGFP fusion protein. The supernatant was discarded and the pellet was resuspended in a 40 mL washing buffer containing 50 mM Tris-HCl (pH 8.0), 100 mM NaCl, 0.1% NaN$_3$, and 0.5% Triton-X100 and centrifuged again (10200 r.p.m., 20 min, 4° C.). After that, the supernatant was discarded and the pellet was then resuspended in the same 40 mL washing buffer without Triton-X100 and centrifuged (10200 r.p.m., 20 min, 4° C.). The process was repeated two more times. A SDS-PAGE analysis showed fairly pure inclusion bodies. The final pellet was resuspended in 8 M urea and then purified using Ni-NTA resins in a denaturing condition. The finally determined expression level of the prolispro-sfGFP fusion protein was 1.5 g/L which corresponded to 350 mg/L of prolispro. A time dependence of the prolispro-sfGFP fusion protein expression was also tested. Cells induced at 4 h and 21 h were collected and their inclusion bodies were then purified. FIG. 5 shows the relative expression levels at two conditions. It is obvious that 21 h induction gave a much higher expression level of the prolispro-sfGFP fusion protein.

Example 10: Processing the Prolispro-sfGFP Fusion Protein to Obtain Mature Lispro To obtain mature lispro, the prolispro-sfGFP fusion protein was refolded using a quick refolding process. The Ni-NTA purified prolispro-sfGFP was stored in 8 M urea and 10 mM Tris-HCl (pH 9.2). A refolding buffer containing 10 mM Tris-HCl (pH 9.2), 10 mM glycine, 1 mM EDTA, and 4.5 mM cystine was then slowly added to the prolispro-sfGFP solution in a 1:1 ratio finally by volume. Next, cysteine was added to the above solution to a final concentration of 0.5 mM and mixed gently by inverting the tubes 2-3 times and the tube was placed in an incubator without agitation for 45 min at 30° C. The presence of cystine and cysteine enables the formation of disulfide bonds for the correct folding of prolispro. Overnight dialysis was then performed to change the buffer of the folded prolispro-sfGFP protein to a digestion buffer (50 mM Tris-HCl, pH 9.0).

Figure 6:
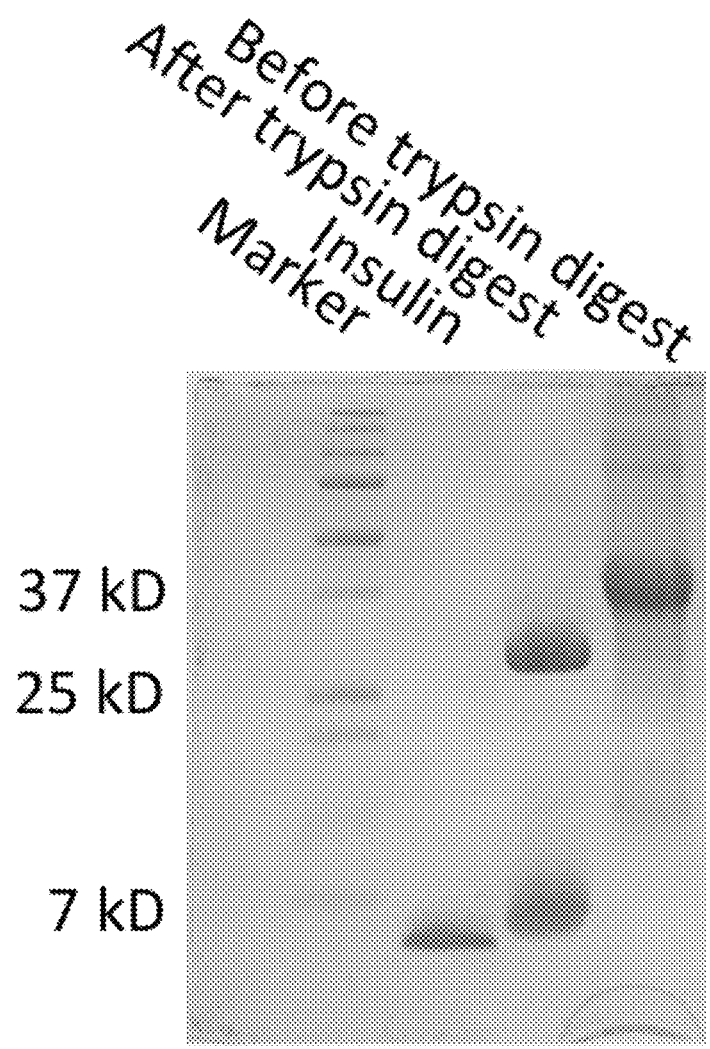
FIG. 6 illustrates a SDS-PAGE of the expressed sfGFP-proinsulin lispro fusion protein after digestion with trypsin and carboxypeptidase B.

After dialysis, the prolispro-sfGFP solution was collected and concentrated to 1 mg/mL and then digested by trypsin (E/S: 1:600, w/w) and carboxypeptidase B (E/S: 1:600, w/w) at 4° C. for 5 h. 0.5 µg/mL leupeptin was then added to terminate the digestion reactions. FIG. 6 is a SDS-PAGE gel that showed the prolispro-sfGFP protein before and after digestion with trypsin and carboxypeptidase B. The gel clearly indicates the desired processing of the prolispro-sfGFP fusion protein to lispro. The lispro band in the gel clearly matched the band of the commercially available insulin. The gel also indicates the correct folding process. Otherwise, trypsin would have recognized the arginine residue in the B chain and gave a much smaller digestion product band.

Figure 7:
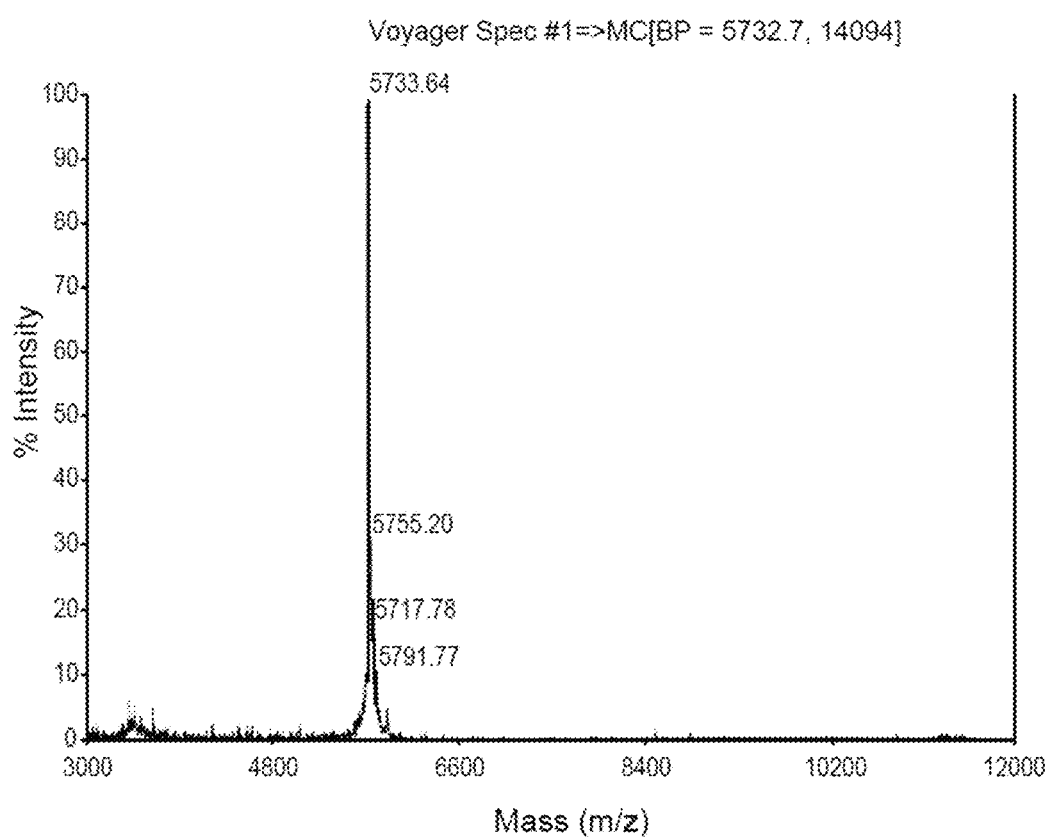
FIG. 7 illustrates a MOLDI-TOF mass spectrometry analysis of the purified lispro.

The trypsin and carboxypeptidase B digested products of the prolispro-sfGFP fusion protein was then dialyzed against a buffer containing 50 mM sodium phosphate (pH 8) and then loaded on a Sephedex G-25 gel filtration column from GE Healthcare. Different digested products were eluted from the column using the same buffer. The fractions containing lispro were collected and concentrated to 1 mg/mL. The finally obtained yield of pure lispro was around 200 mg/L. The purified lispro was also subjected to the MALDI-TOF mass spectrometry analysis. The detected molecular weight shown in FIG. 7 was 5733.6 Da that agreed well with the theoretical molecular weight (5733 Da).

Example 11: Expression of the Proinsulin-sfGFP Fusion Protein

To express the proinsulin-sfGFP fusion protein, a sequence confirmed psfGFPN-proinsulin plasmid was used to chemically transform E. coli Top10 cells. The transformed cells were grown on a LB plate containing 100 µg/mL ampicillin overnight. A single colony was selected to grow in a 5 mL LB culture containing 100 µg/mL ampicillin overnight. This overnight culture was then used to inoculate a 1 L 2YT medium containing µg/mL ampicillin and grown at 37° C. until the OD$_{600}$ was 0.7. A 20% arabinose solution was then added to the medium to final concentration of 0.2% to induce the expression of the fusion protein. The following purification procedures of the expressed fusion protein from the inclusion bodies were as same as those for the prolispro-sfGFP fusion protein. The finally determined expression level of the proinsulin-sfGFP fusion protein was 145 mg/L that corresponded to around 350 mg/L expression level of proinsulin.

Example 12: Expression of the Proglargine-sfGFP Fusion Protein

To express the proglargine-sfGFP fusion protein, a sequence confirmed psfGFPN-proglargine plasmid was used to chemically transform E. coli Top10 cells. The transformed cells were grown on a LB plate containing 100 µg/mL ampicillin overnight. A single colony was selected to grow in a 5 mL LB culture containing 100 µg/mL ampicillin overnight. This overnight culture was then used to inoculate a 1 L 2YT medium containing µg/mL ampicillin and grown at 37° C. until the OD$_{600}$ was 0.7. A 20% arabinose solution was then added to the medium to final concentration of 0.2% to induce the expression of the fusion protein. The following purification procedures of the expressed fusion protein from the inclusion bodies were as same as those for the prolispro-sfGFP fusion protein. The finally determined expression level of the proglargine-sfGFP fusion protein was 140 mg/L that corresponded to around 345 mg/L expression level of proinsulin.

Example 13: Expression of the sfGFP-PTH Fusion Protein

To express the sfGFP-PTH fusion protein, a sequence confirmed psfGFPC-PTH plasmid was used to chemically transform E. coli Top10 cells. The transformed cells were grown on a LB plate containing 100 µg/mL ampicillin overnight. A single colony was selected to grow in a 5 mL LB culture containing 100 µg/mL ampicillin overnight. This overnight culture was then used to inoculate a 1 L 2YT medium containing µg/mL ampicillin and grown at 37° C. until the OD$_{600}$ was 0.7. A 20% arabinose solution was then added to the medium to final concentration of 0.2% to induce the expression of the fusion protein. The cells were grown for an additional 16 hours and then collected by centrifugation (4500 r.p.m., 20 min, 4° C.).

Figure 8:
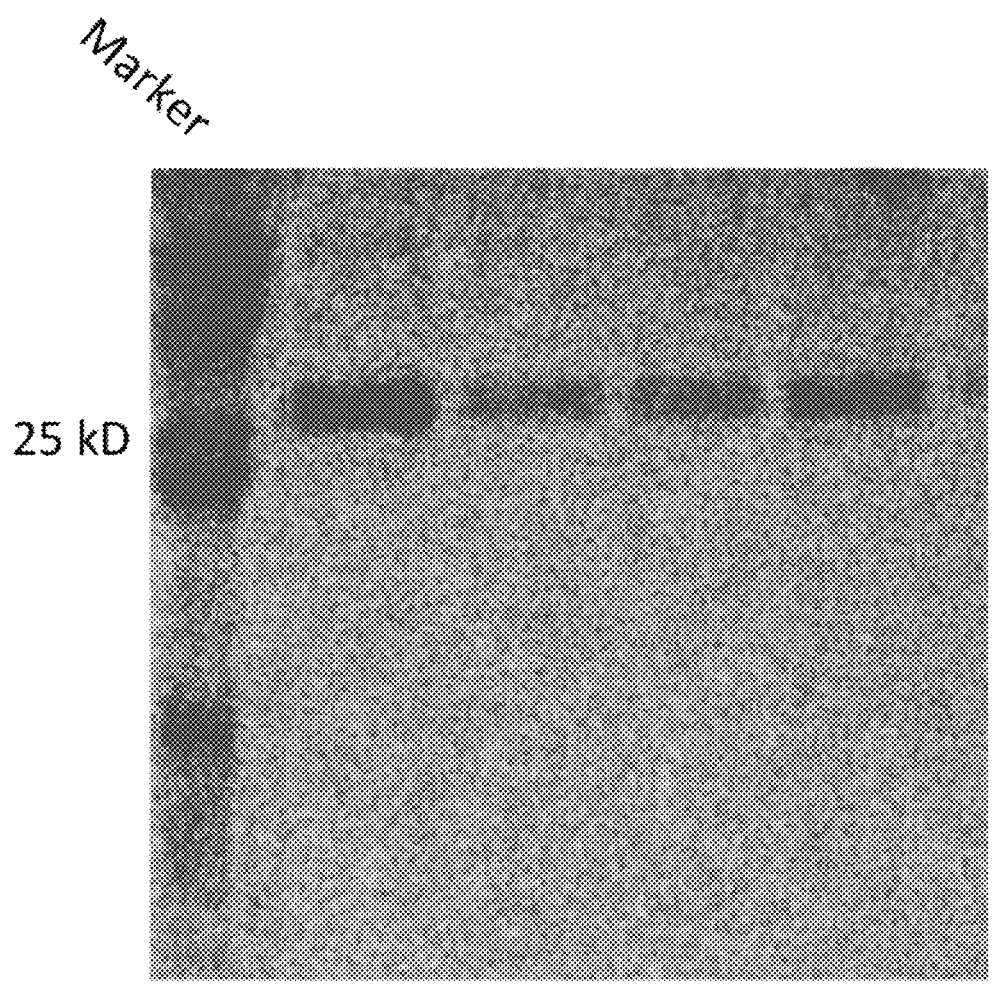
FIG. 8 illustrates a SDS-PAGE of the expressed sfGFP-PTH fusion protein.

The collected cells were re-suspended in 20 mL of lysis buffer (50 mM HEPES, pH 7.4, 500 mM NaCl, 10 mM DTT, 10% glycerol, 0.1% Triton X-100, 5 mM imidazole, and 1 µg/mL lysozyme). The resuspended cells were sonicated and the lysate was clarified by centrifugation (10200 r.p.m., 60 min, 4° C.). The following SDS-PAGE analysis of the supernatant and the cell debris indicating part of the fusion protein was expressed in the cytoplasm in a soluble form and part of the fusion protein was expressed in inclusion bodies in an insoluble form. Because of the easy processing of the soluble protein, we let the supernatant mix with Ni-NTA resins and purified the soluble fusion protein by eluting the resins with the lysis buffer with 250 mM imidazole. FIG. 8 shows the different fractions of the sfGFP-PTH fusion protein eluted from Ni-NTA resins indicating high purity. The determined expression yield of the finally obtained sfGFP-PTH fusion was 600 mg/L that corresponded to 60 mg/L expression level for PTH itself. Given that part of the fusion protein was in the inclusion bodies, the real expression levels of the sfGFP-PTH fusion protein and PTH were higher. The purified sfGFP-PTH fusion was also digested by TEV protease to release PTH. The digested products were further separated using reverse phase HPLC on a C18 column using an acetonitrile-water gradient containing 0.1% TFA to obtain pure PTH.

Example 14: Expression of the sfGFP-Calcitonin Fusion Protein

To express the sfGFP-calcitonin fusion protein, a sequence confirmed psfGFPC-calcitonin plasmid was used to chemically transform *E. coli* Top10 cells. The transformed cells were grown on a LB plate containing 100 µg/mL ampicillin overnight. A single colony was selected to grow in a 5 mL LB culture containing 100 µg/mL ampicillin overnight. This overnight culture was then used to inoculate a 1 L 2YT medium containing µg/mL ampicillin and grown at 37° C. until the $OD_{600}$ was 0.7. A 20% arabinose solution was then added to the medium to final concentration of 0.2% to induce the expression of the fusion protein. The cells were grown for an additional 16 hours and then collected by centrifugation (4500 r.p.m., 20 min, 4° C.).

Figure 9:
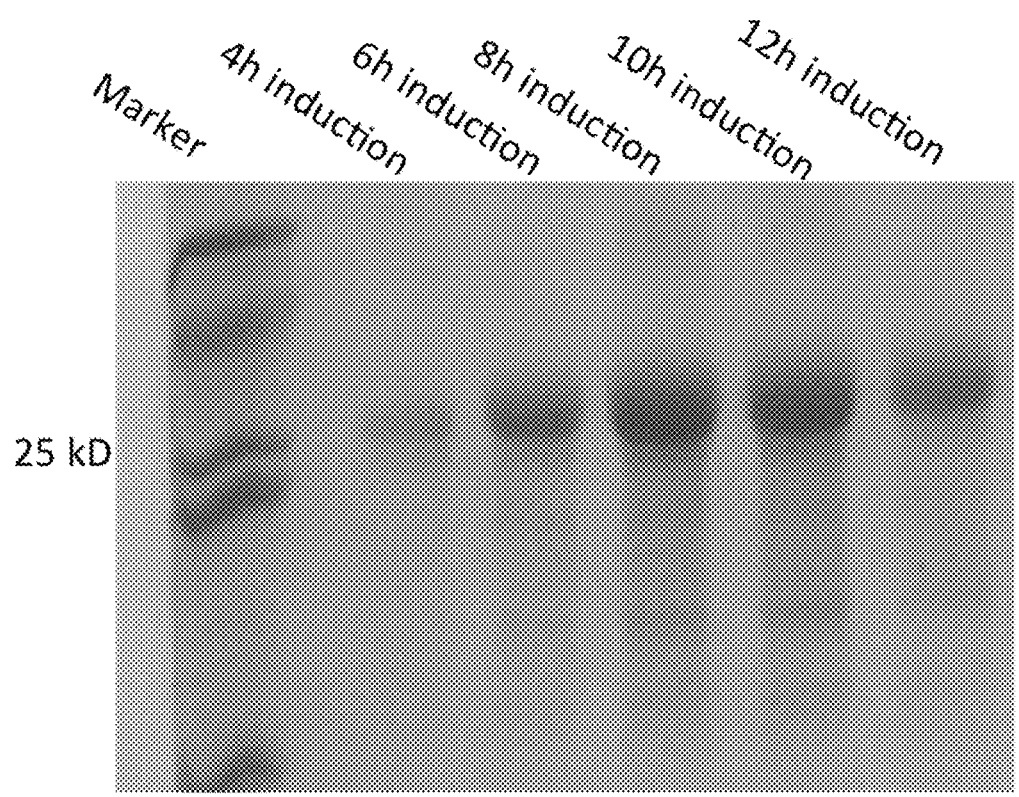
FIG. 9 illustrates a SDS-PAGE of the expressed sfGFP-Calcitonin fusion protein.

The collected cells were re-suspended in 20 mL of lysis buffer (50 mM HEPES, pH 7.4, 500 mM NaCl, 10 mM DTT, 10% glycerol, 0.1% Triton X-100, 5 mM imidazole, and 1 µg/mL lysozyme). The resuspended cells were sonicated and the lysate was clarified by centrifugation (10200 r.p.m., 60 min, 4° C.). Similarly as PTH, the following SDS-PAGE analysis of the supernatant and the cell debris indicating part of the fusion protein was expressed in the cytoplasm in a soluble form and part of the fusion protein was expressed in inclusion bodies in an insoluble form. We processed the purification of the fusion protein from the supernatant. The supernatant was mix with Ni-NTA resins and purified the soluble fusion protein by eluting the resins with the lysis buffer with 250 mM imidazole. The determined expression yield of the finally obtained sfGFP-PTH fusion was 500 mg/L that corresponded to 50 mg/L expression level for calcitonin itself. The induction time dependence of the fusion protein expression was also analyzed by collecting cells at different times and analyzing the purified fusion protein from the cytoplasm. FIG. 9 shows the expression level peaked around 8-10 h induction. The purified sfGFP-calcitonin fusion was also digested by TEV protease to release calcitonin. The digested products were further separated using reverse phase HPLC on a C18 column using an acetonitrile-water gradient containing 0.1% TFA to obtain pure calcitonin.

Example 15: Expression of GLP-1

To express the sfGFP-GLP-1 fusion protein, a sequence confirmed psfGFPC-GLP1 plasmid was used to chemically transform *E. coli* Top10 cells. The transformed cells were grown on a LB plate containing 100 µg/mL ampicillin overnight. A single colony was selected to grow in a 5 mL LB culture containing 100 µg/mL ampicillin overnight. This overnight culture was then used to inoculate a 1 L 2YT medium containing µg/mL ampicillin and grown at 37° C. until the $OD_{600}$ was 0.7. A 20% arabinose solution was then added to the medium to final concentration of 0.2% to induce the expression of the fusion protein. The cells were grown for an additional 16 hours and then collected by centrifugation (4500 r.p.m., 20 min, 4° C.).

Figure 10:
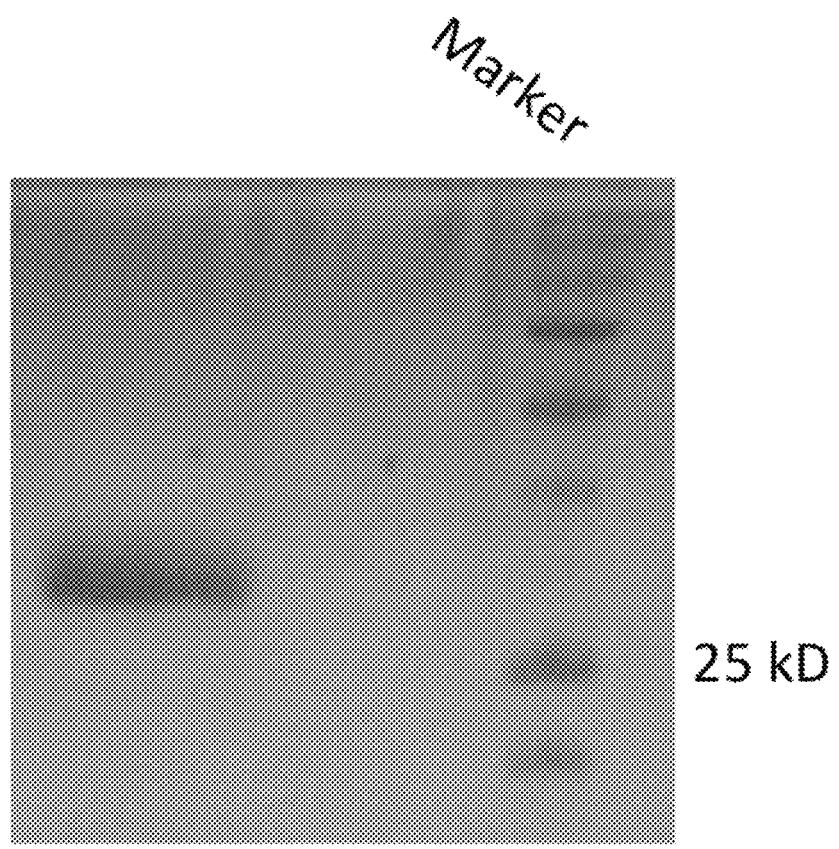
FIG. 10 illustrates a SDS-PAGE of the expressed sfGFP-GLP1 fusion protein.

The collected cells were re-suspended in 20 mL of lysis buffer (50 mM HEPES, pH 7.4, 500 mM NaCl, 10 mM DTT, 10% glycerol, 0.1% Triton X-100, 5 mM imidazole, and 1 µg/mL lysozyme). The resuspended cells were sonicated and the lysate was clarified by centrifugation (10200 r.p.m., 60 min, 4° C.). Similarly as PTH and calcitonin, the following SDS-PAGE analysis of the supernatant and the cell debris indicating part of the sfGFP-GLP-1 fusion protein was expressed in the cytoplasm in a soluble form and part of the fusion protein was expressed in inclusion bodies in an insoluble form. We processed the purification of the fusion protein from the supernatant. The supernatant was mix with Ni-NTA resins and purified the soluble fusion protein by eluting the resins with the lysis buffer with 250 mM imidazole. A SDS-PAGE analysis of the purified fusion protein shown in FIG. 10 indicated high purity. The determined expression yield of the finally obtained sfGFP-GLP-1 fusion was 500 mg/L that corresponded to 65 mg/L expression level for GLP-1 itself. The purified sfGFP-GLP-1 fusion was also digested by TEV protease to release calcitonin. The digested products were further separated using reverse phase HPLC on a C18 column using an acetonitrile-water gradient containing 0.1% TFA to obtain pure calcitonin.

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

APPENDIX

AMINO ACID AND NUCLEOTIDE SEQUENCES

| | SEQUENCE |
|---|---|
| SEQ ID NO: 1 Superfolder green fluorescent protein one-letter amino acid sequence | SKGEELFTGVVPILVELDGDVNGHKFSVRGEGEGDATNGK LTLKFICTTGKLPVPWPTLVTTLTYGVQCFSRYPDHMKRH DFFKSAMPEGYVQERTISFKDDGTYKTRAEVKFEGDTLVN RIELKGIDFKEDGNILGHKLEYNFNSHNVYITADKQKNGI KANFKIRHNVEDGSVQLADHYQQNTPIGDGPVLLPDNHYL STQSVLSKDPNEKRDHMVLLEFVTAAGITHGMDELYK |
| SEQ ID NO: 2 Superfolder green fluorescent protein nucleotide sequence | AGCAAAGGTGAAGAACTGTTTACCGGCGTTGTGCCGATTCT GGTGGAACTGGATGGTGATGTGAATGGCCATAAATTTAGCG TTCGTGGCGAAGGCGAAGGTGATGCGACCAACGGTAAACTG ACCCTGAAATTTATTTGCACCACCGGTAAACTGCCGGTTCCG TGGCCGACCCTGGTGACCACCCTGACCTATGGCGTTCAGTG CTTTAGCCGCTATCCGGATCATATGAAACGCCATGATTTCTT TAAAAGCGCGATGCCGGAAGGCTATGTGCAGGAACGTACC ATTAGCTTCAAAGATGATGGCACCTATAAAACCCGTGCGGA AGTTAAATTTGAAGGCGATACCCTGGTGAACCGCATTGAAC TGAAAGGTATTGATTTTAAAGAAGATGGCAACATTCTGGGT CATAAACTGGAATATAATTTCAACAGCCATAATGTGTATAT TACCGCCGATAAACAGAAAAATGGCATCAAAGCGAACTTTA AAATCCGTCACAACGTGGAAGATGGTAGCGTGCAGCTGGCG GATCATTATCAGCAGAATACCCCGATTGGTGATGGCCCGGT GCTGCTGCCGGATAATCATTATCTGAGCACCCAGAGCGTTC TGAGCAAAGATCCGAATGAAAAACGTGATCATATGGTGCTG CTGGAATTTGTTACCGCCGCGGGCATTACCCACGGTATGGA TGAACTGTATAAAG |
| SEQ ID NO: 3 one-letter amino acid sequence of a TEV cleavage site | ENLYFQG |
| SEQ ID NO: 4 nucleotide sequence of a TEV cleavage site | GAAAACCTGTATTTTCAGGGA |
| SEQ ID NO: 5 one-letter amino acid sequence of another TEV cleavage site | ENLYFQS |
| SEQ ID NO: 6 nucleotide sequence of another TEV cleavage site | GAAAACCTGTATTTTCAGTCT |
| SEQ ID NO: 7 prolispro one-letter amino acid sequence | FVNQHLCGSHLVEALYLVCGERGFFYTKPTRREAEDLQVGQV ELGGGPGAGSLQPLALEGSLQKRGIVEQCCTSICSLYQLENYCN |
| SEQ ID NO: 8 prolispro nucleotide sequence | TTCGTTAACCAACACCTGTGCGGCAGCCACCTGGTAGAGGC ACTGTATCTGGTTTGTGGTGAACGTGGCTTCTTCTATACTAA ACCGACTCGTCGCGAAGCAGAGGATCTGCAAGTGGGTCAGG TTGAGCTGGGCGGTGGTCCGGGTGCTGGCTCCCTGCAACCG CTGGCGCTGGAGGGTTCCCTGCAAAAGCGTGGTATCGTGGA ACAGTGTTGCACTTCTATTTGCTCTCTGTATCAGCTGGAAAA TTACTGTAAT |
| SEQ ID NO: 9 prolispro-sfGFP fusion protein one-letter amino acid sequence | MARFVNQHLCGSHLVEALYLVCGERGFFYTKPTRREAEDLQV GQVELGGGPGAGSLQPLALEGSLQKRGIVEQCCTSICSLYQLE NYCNRENLYFQGAMVSKGEELFTGVVPILVELDGDVNGHKFS VRGEGEGDATNGKLTLKFICTTGKLPVPWPTLVTTLTYGVQCF SRYPDHMKRHDFFKSAMPEGYVQERTISFKDDGTYKTRAEVK FEGDTLVNRIELKGIDFKEDGNILGHKLEYNFNSHNVYITADKQ KNGIKANFKIRHNVEDGSVQLADHYQQNTPIGDGPVLLPDNH YLSTQSVLSKDPNEKRDHMVLLEFVTAAGITHGMDELYKGSH HHHHH |
| SEQ ID NO: 10 prolispro-sfGFP fusion protein nucleotide sequence | ATGGCGCGTTTCGTTAACCAACACCTGTGCGGCAGCCACCT GGTAGAGGCACTGTATCTGGTTTGTGGTGAACGTGGCTTCTT CTATACTAAACCGACTCGTCGCGAAGCAGAGGATCTGCAAG TGGGTCAGGTTGAGCTGGGCGGTGGTCCGGGTGCTGGCTCC CTGCAACCGCTGGCGCTGGAGGGTTCCCTGCAAAAGCGTGG TATCGTGGAACAGTGTTGCACTTCTATTTGCTCTCTGTATCA GCTGGAAAATTACTGTAATCGTGAAAACCTGTATTTTCAGG GAGCCATGGTTTCTAAAGGTGAAGAACTTTTTACTGGTGTTG TTCCTATTCTTGTTGAACTTGATGGTGATGTTAATGGTCATA |

APPENDIX-continued

AMINO ACID AND NUCLEOTIDE SEQUENCES

| | SEQUENCE |
|---|---|
| | AATTTTCTGTTCGTGGTGAAGGTGAAGGTGATGCTACTAAT<br>GGTAAACTTACTCTTAAATTTATTTGTACTACTGGTAAACTT<br>CCTGTTCCTTGGCCTACTCTTGTTACTACTCTTACTTATGGTG<br>TTCAATGTTTTTCTCGTTATCCTGATCATATGAAACGTCATG<br>ATTTTTTTAAATCTGCTATGCCTGAAGGTTATGTTCAAGAAC<br>GTACTATTTCTTTTAAAGATGATGGTACTTATAAAACTCGTG<br>CTGAAGTTAAATTTGAAGGTGATACTCTTGTTAATCGTATTG<br>AACTTAAAGGTATTGATTTTAAAGAAGATGGTAATATTCTT<br>GGTCATAAACTTGAATATAATTTTAATTCTCATAATGTTTAT<br>ATTACTGCTGATAAACAAAAAAATGGTATTAAAGCTAATTT<br>TAAAATTCGTCATAATGTTGAAGATGGTTCTGTTCAACTTGC<br>TGATCATTATCAACAAAATACTCCTATTGGTGATGGTCCTGT<br>TCTTCTTCCTGATAATCATTATCTTTCTACTCAATCTGTTCTT<br>TCTAAAGATCCTAATGAAAAACGTGATCATATGGTTCTTCTT<br>GAATTTGTTACTGCTGCTGGTATTACTCATGGTATGGATGAA<br>CTTTATAAAGGTTCTCATCATCATCATCATCAT |
| SEQ ID NO: 11<br>proinsulin one-letter<br>amino acid sequence | FVNQHLCGSHLVEALYLVCGERGFFYTPKTRREAEDLQVGQV<br>ELGGGPGAGSLQPLALEGSLQKRGIVEQCCTSICSLYQLENYCN |
| SEQ ID NO: 12<br>proinsulin nucleotide<br>sequence | TTCGTTAACCAACACCTGTGCGGCAGCCACCTGGTAGAGGC<br>ACTGTATCTGGTTTGTGGTAACGTGGCTTCTTCTATACTCC<br>GAAAACTCGTCGCGAAGCAGAGGATCTGCAAGTGGGTCAG<br>GTTGAGCTGGGCGGTGGTCCGGGTGCTGGCTCCCTGCAACC<br>GCTGGCGCTGGAGGGTTCCCTGCAAAAGCGTGGTATCGTGG<br>AACAGTGTTGCACTTCTATTTGCTCTCTGTATCAGCTGGAAA<br>ATTACTGTAAT |
| SEQ ID NO: 13<br>proinsulin-sfGFP<br>fusion protein one-letter<br>amino acid sequence | MARFVNQHLCGSHLVEALYLVCGERGFFYTPKTRREAEDLQV<br>GQVELGGGPGAGSLQPLALEGSLQKRGIVEQCCTSICSLYQLE<br>NYCNRENLYFQGAMVSKGEELFTGVVPILVELDGDVNGHKFS<br>VRGEGEGDATNGKLTLKFICTTGKLPVPWPTLVTTLTYGVQCF<br>SRYPDHMKRHDFFKSAMPEGYVQERTISFKDDGTYKTRAEVK<br>FEGDTLVNRIELKGIDFKEDGNILGHKLEYNFNSHNVYITADKQ<br>KNGIKANFKIRHNVEDGSVQLADHYQQNTPIGDGPVLLPDNH<br>YLSTQSVLSKDPNEKRDHMVLLEFVTAAGITHGMDELYKGSH<br>HHHHH |
| SEQ ID NO: 14<br>proinsulin-sfGFP<br>fusion protein<br>nucleotide sequence | ATGGCGCGTTTCGTTAACCAACACCTGTGCGGCAGCCACCT<br>GGTAGAGGCACTGTATCTGGTTTGTGGTAACGTGGCTTCTT<br>CTATACTCCGAAAACTCGTCGCGAAGCAGAGGATCTGCAAG<br>TGGGTCAGGTTGAGCTGGGCGGTGGTCCGGGTGCTGGCTCC<br>CTGCAACCGCTGGCGCTGGAGGGTTCCCTGCAAAAGCGTGG<br>TATCGTGGAACAGTGTTGCACTTCTATTTGCTCTCTGTATCA<br>GCTGGAAAATTACTGTAATCGTGAAAACCTGTATTTTCAGG<br>GAGCCATGGTTTCTAAAGGTGAAGAACTTTTTACTGGTGTTG<br>TTCCTATTCTTGTTGAACTTGATGGTGATGTTAATGGTCATA<br>AATTTTCTGTTCGTGGTGAAGGTGAAGGTGATGCTACTAAT<br>GGTAAACTTACTCTTAAATTTATTTGTACTACTGGTAAACTT<br>CCTGTTCCTTGGCCTACTCTTGTTACTACTCTTACTTATGGTG<br>TTCAATGTTTTTCTCGTTATCCTGATCATATGAAACGTCATG<br>ATTTTTTTAAATCTGCTATGCCTGAAGGTTATGTTCAAGAAC<br>GTACTATTTCTTTTAAAGATGATGGTACTTATAAAACTCGTG<br>CTGAAGTTAAATTTGAAGGTGATACTCTTGTTAATCGTATTG<br>AACTTAAAGGTATTGATTTTAAAGAAGATGGTAATATTCTT<br>GGTCATAAACTTGAATATAATTTTAATTCTCATAATGTTTAT<br>ATTACTGCTGATAAACAAAAAAATGGTATTAAAGCTAATTT<br>TAAAATTCGTCATAATGTTGAAGATGGTTCTGTTCAACTTGC<br>TGATCATTATCAACAAAATACTCCTATTGGTGATGGTCCTGT<br>TCTTCTTCCTGATAATCATTATCTTTCTACTCAATCTGTTCTT<br>TCTAAAGATCCTAATGAAAAACGTGATCATATGGTTCTTCTT<br>GAATTTGTTACTGCTGCTGGTATTACTCATGGTATGGATGAA<br>CTTTATAAAGGTTCTCATCATCATCATCATCAT |
| SEQ ID NO: 15<br>proglargine one-letter<br>amino acid sequence | FVNQHLCGSHLVEALYLVCGERGFFYTPKTRREAEDLQVGQV<br>ELGGGPGAGSLQPLALEGSLQKRGIVEQCCTSICSLYQLENYCG |
| SEQ ID NO: 16<br>proglargine nucleotide<br>sequence | TTCGTTAACCAACACCTGTGCGGCAGCCACCTGGTAGAGGC<br>ACTGTATCTGGTTTGTGGTAACGTGGCTTCTTCTATACTCC<br>GAAAACTCGTCGCGAAGCAGAGGATCTGCAAGTGGGTCAG<br>GTTGAGCTGGGCGGTGGTCCGGGTGCTGGCTCCCTGCAACC<br>GCTGGCGCTGGAGGGTTCCCTGCAAAAGCGTGGTATCGTGG<br>AACAGTGTTGCACTTCTATTTGCTCTCTGTATCAGCTGGAAA<br>ATTACTGTGGC |

APPENDIX-continued

AMINO ACID AND NUCLEOTIDE SEQUENCES

| | SEQUENCE |
|---|---|
| SEQ ID NO: 17 proglargine-sfGFP fusion protein one-letter amino acid sequence | MARFVNQHLCGSHLVEALYLVCGERGFFYTPKTRREAEDLQV GQVELGGGPGAGSLQPLALEGSLQKRGIVEQCCTSICSLYQLE NYCGRENLYFQGAMVSKGEELFTGVVPILVELDGDVNGHKFS VRGEGEGDATNGKLTLKFICTTGKLPVPWPTLVTTLTYGVQCF SRYPDHMKRHDFFKSAMPEGYVQERTISFKDDGTYKTRAEVK FEGDTLVNRIELKGIDFKEDGNILGHKLEYNFNSHNVYITADKQ KNGIKANFKIRHNVEDGSVQLADHYQQNTPIGDGPVLLPDNH YLSTQSVLSKDPNEKRDHMVLLEFVTAAGITHGMDELYKGSH HHHHH |
| SEQ ID NO: 18 proglargine-sfGFP fusion protein nucleotide sequence | ATGGCGCGTTTCGTTAACCAACACCTGTGCGGCAGCCACCT GGTAGAGGCACTGTATCTGGTTTGTGGTGAACGTGGCTTCTT CTATACTCCGAAAACTCGTCGCGAAGCAGAGGATCTGCAAG TGGGTCAGGTTGAGCTGGGCGGTGGTCCGGGTGCTGGCTCC CTGCAACCGCTGGCGCTGGAGGGTTCCCTGCAAAAGCGTGG TATCGTGGAACAGTGTTGCACTTCTATTTGCTCTCTGTATCA GCTGGAAAATTACTGTGGCCGTGAAAACCTGTATTTTCAGG GAGCCATGGTTTCTAAAGGTGAAGAACTTTTTACTGGTGTTG TTCCTATTCTTGTTGAACTTGATGGTGATGTTAATGGTCATA AATTTTCTGTTCGTGGTGAAGGTGAAGGTGATGCTACTAAT GGTAAACTTACTCTTAAATTTATTTGTACTACTGGTAAACTT CCTGTTCCTTGGCCTACTCTTGTTACTACTCTTACTTATGGTG TTCAATGTTTTTCTCGTTATCCTGATCATATGAAACGTCATG ATTTTTTTAAATCTGCTATGCCTGAAGGTTATGTTCAAGAAC GTACTATTTCTTTTAAAGATGATGGTACTTATAAAACTCGTG CTGAAGTTAAATTTGAAGGTGATACTCTTGTTAATCGTATTG AACTTAAAGGTATTGATTTTAAAGAAGATGGTAATATTCTT GGTCATAAACTTGAATATAATTTTAATTCTCATAATGTTTAT ATTACTGCTGATAAACAAAAAAATGGTATTAAAGCTAATTT TAAAATTCGTCATAATGTTGAAGATGGTTCTGTTCAACTTGC TGATCATTATCAACAAAATACTCCTATTGGTGATGGTCCTGT TCTTCTTCCTGATAATCATTATCTTTCTACTCAATCTGTTCTT TCTAAAGATCCTAATGAAAAACGTGATCATATGGTTCTTCTT GAATTTGTTACTGCTGCTGGTATTACTCATGGTATGGATGAA CTTTATAAAGGTTCTCATCATCATCATCATCAT |
| SEQ ID NO: 19 PTH one-letter amino acid sequence | SVSEIQLMHNLGKHLNSMERVEWLRKKLQDVHNF |
| SEQ ID NO: 20 PTH nucleotide sequence | TCTGTTTCTGAAATCCAGCTGATGCACAACCTGGGTAAACA CCTGAACTCTATGGAACGTGTTGAATGGCTGCGTAAAAAAC TGCAGGACGTTCACAACTTC |
| SEQ ID NO: 21 sfGFP-PTH fusion protein one-letter amino acid sequence | MVHHHHHHAASKGEELFTGVVPILVELDGDVNGHKFSVRGEG EGDATNGKLTLKFICTTGKLPVPWPTLVTTLTYGVQCFSRYPD HMKRHDFFKSAMPEGYVQERTISFKDDGTYKTRAEVKFEGDT LVNRIELKGIDFKEDGNILGHKLEYNFNSHNVYITADKQKNGIK ANFKIRHNVEDGSVQLADHYQQNTPIGDGPVLLPDNHYLSTQS VLSKDPNEKRDHMVLLEFVTAAGITHGMDELYKARDENLYFQ SVSEIQLMHNLGKHLNSMERVEWLRKKLQDVHNF |
| SEQ ID NO: 22 sfGFP-PTH fusion protein nucleotide sequence | ATGGTTCACCATCATCATCACCATGCGGCGAGCAAAGGTGA AGAACTGTTTACCGGCGTTGTGCCGATTCTGGTGGAACTGG ATGGTGATGTGAATGGCCATAAATTTAGCGTTCGTGGCGAA GGCGAAGGTGATGCGACCAACGGTAAACTGACCCTGAAATT TATTTGCACCACCGGTAAACTGCCGGTTCCGTGGCCGACCCT GGTGACCACCCTGACCTATGGCGTTCAGTGCTTTAGCCGCTA TCCGGATCATATGAAACGCCATGATTTCTTTAAAAGCGCGA TGCCGGAAGGCTATGTGCAGGAACGTACCATTAGCTTCAAA GATGATGGCACCTATAAACCCGTGCGGAAGTTAAATTTGA AGGCGATACCCTGGTGAACCGCATTGAACTGAAAGGTATTG ATTTTAAAGAAGATGGCAACATTCTGGGTCATAAACTGGAA TATAATTTCAACAGCCATAATGTGTATATTACCGCCGATAA ACAGAAAAATGGCATCAAAGCGAACTTTAAAATCCGTCACA ACGTGGAAGATGGTAGCGTGCAGCTGGCGGATCATTATCAG CAGAATACCCCGATTGGTGATGGCCCGGTGCTGCTGCCGGA TAATCATTATCTGAGCACCCAGAGCGTTCTGAGCAAAGATC CGAATGAAAAACGTGATCATATGGTGCTGCTGGAATTTGTT ACCGCCGCGGGCATTACCCACGGTATGGATGAACTGTATAA AGCTCGAGATGAAAACCTGTATTTTCAGTCTGTTTCTGAAAT CCAGCTGATGCACAACCTGGGTAAACACCTGAACTCTATGG AACGTGTTGAATGGCTGCGTAAAAAAACTGCAGGACGTTCAC AACTTC |

APPENDIX-continued

AMINO ACID AND NUCLEOTIDE SEQUENCES

| | SEQUENCE |
|---|---|
| SEQ ID NO: 23 calcitonin one-letter amino acid sequence | CSNLSTCVLGKLSQELHKLQTYPRTNTGSGTP |
| SEQ ID NO: 24 calcitonin nucleotide sequence | TGCTCTGCGCTGTCTACCTGCGTTCTGGGTCTGCTGTCTGGT GGTCTGCACCTGCTGGGTACCACCCCGGCGACCGCGACCGG TTCTGGTACCCCG |
| SEQ ID NO: 25 sfGFP-calcitonin one-letter amino acid sequence | MVHHHHHHAASKGEELFTGVVPILVELDGDVNGHKFSVRGEG EGDATNGKLTLKFICTTGKLPVPWPTLVTTLTYGVQCFSRYPD HMKRHDFFKSAMPEGYVQERTISFKDDGTYKTRAEVKFEGDT LVNRIELKGIDFKEDGNILGHKLEYNFNSHNVYITADKQKNGIK ANFKIRHNVEDGSVQLADHYQQNTPIGDGPVLLPDNHYLSTQS VLSKDPNEKRDHMVLLEFVTAAGITHGMDELYKARDENLYFQ CSALSTCVLGLLSGGLHLLGTTPATATGSGTP |
| SEQ ID NO: 26 sfGFP-calcitonin nucleotide sequence | ATGGTTCACCATCATCATCACCATGCGGCGAGCAAAGGTGA AGAACTGTTTACCGGCGTTGTGCCGATTCTGGTGGAACTGG ATGGTGATGTGAATGGCCATAAATTTAGCGTTCGTGGCGAA GGCGAAGGTGATGCGACCAACGGTAAACTGACCCTGAAATT TATTTGCACCACCGGTAAACTGCCGGTTCCGTGGCCGACCCT GGTGACCACCCTGACCTATGGCGTTCAGTGCTTTAGCCGCTA TCCGGATCATATGAAACGCCATGATTTCTTTAAAAGCGCGA TGCCGGAAGGCTATGTGCAGGAACGTACCATTAGCTTCAAA GATGATGGCACCTATAAAACCCGTGCGGAAGTTAAATTTGA AGGCGATACCCTGGTGAACCGCATTGAACTGAAAGGTATTG ATTTTAAAGAAGATGGCAACATTCTGGGTCATAAACTGGAA TATAATTTCAACAGCCATAATGTGTATATTACCGCCGATAA ACAGAAAAATGGCATCAAAGCGAACTTTAAAATCCGTCACA ACGTGGAAGATGGTAGCGTGCAGCTGGCGGATCATTATCAG CAGAATACCCCGATTGGTGATGGCCCGGTGCTGCTGCCGGA TAATCATTATCTGAGCACCCAGAGCGTTCTGAGCAAAGATC CGAATGAAAAACGTGATCATATGGTGCTGCTGGAATTTGTT ACCGCCGCGGGCATTACCCACGGTATGGATGAACTGTATAA AGCTCGAGATGAAAACCTGTATTTTCAGTGCTCTGCGCTGTC TACCTGCGTTCTGGGTCTGCTGTCTGGTGGTCTGCACCTGCT GGGTACCACCCCGGCGACCGCGACCGGTTCTGGTACCCCG |
| SEQ ID NO: 27 GLP-1 one-letter amino acid sequence | HGEGTFTSDLSKQMEEEAVRLFIEWLKNGGPSSGAPPPS |
| SEQ ID NO: 28 GLP-1 nucleotide sequence | CACGGTGGTGGTACCCCGACCTCTGCGCTGTCTCTGGGTATG GGTGGTGGTGCGGTTGCG CTGCCGATCGGTACCCTGCTGGCGGGTGGTCCGTCTTCTGGT GCGCCGCCGCCGTCT |
| SEQ ID NO: 29 sfGFP-GLP-1 one-letter amino acid sequence | MVHHHHHHAASKGEELFTGVVPILVELDGDVNGHKFSVRGEG EGDATNGKLTLKFICTTGKLPVPWPTLVTTLTYGVQCFSRYPD HMKRHDFFKSAMPEGYVQERTISFKDDGTYKTRAEVKFEGDT LVNRIELKGIDFKEDGNILGHKLEYNFNSHNVYITADKQKNGIK ANFKIRHNVEDGSVQLADHYQQNTPIGDGPVLLPDNHYLSTQS VLSKDPNEKRDHMVLLEFVTAAGITHGMDELYKARDENLYFQ HGGGTPTSALSLGMGGGAVALPIGTLLAGGPSSGAPPPS |
| SEQ ID NO: 30 sfGFP-GLP-1 nucleotide sequence | ATGGTTCACCATCATCATCACCATGCGGCGAGCAAAGGTGA AGAACTGTTTACCGGCGTTGTGCCGATTCTGGTGGAACTGG ATGGTGATGTGAATGGCCATAAATTTAGCGTTCGTGGCGAA GGCGAAGGTGATGCGACCAACGGTAAACTGACCCTGAAATT TATTTGCACCACCGGTAAACTGCCGGTTCCGTGGCCGACCCT GGTGACCACCCTGACCTATGGCGTTCAGTGCTTTAGCCGCTA TCCGGATCATATGAAACGCCATGATTTCTTTAAAAGCGCGA TGCCGGAAGGCTATGTGCAGGAACGTACCATTAGCTTCAAA GATGATGGCACCTATAAAACCCGTGCGGAAGTTAAATTTGA AGGCGATACCCTGGTGAACCGCATTGAACTGAAAGGTATTG ATTTTAAAGAAGATGGCAACATTCTGGGTCATAAACTGGAA TATAATTTCAACAGCCATAATGTGTATATTACCGCCGATAA ACAGAAAAATGGCATCAAAGCGAACTTTAAAATCCGTCACA ACGTGGAAGATGGTAGCGTGCAGCTGGCGGATCATTATCAG CAGAATACCCCGATTGGTGATGGCCCGGTGCTGCTGCCGGA TAATCATTATCTGAGCACCCAGAGCGTTCTGAGCAAAGATC CGAATGAAAAACGTGATCATATGGTGCTGCTGGAATTTGTT ACCGCCGCGGGCATTACCCACGGTATGGATGAACTGTATAA |

APPENDIX-continued

AMINO ACID AND NUCLEOTIDE SEQUENCES

SEQUENCE

AGCTCGAGATGAAAACCTGTATTTTCAGCACGGTGGTGGTA
CCCCGACCTCTGCGCTGTCTCTGGGTATGGGTGGTGGTGCG
GTTGCGCTGCCGATCGGTACCCTGCTGGCGGGTGGTCCGTCT
TCTGGTGCGCCGCCGCCGTCT

What is claimed is:

1. A method for enhancing expression of a target peptide, the method comprising culturing a host cell transformed with an expression vector comprising a nucleic acid encoding a fusion protein that comprises a fusion carrier protein linked to the target peptide, wherein the fusion carrier protein has an amino acid sequence as set forth in Formula $$T1-A1-T2 \qquad (I),$$

wherein

T1 is absent, a Met, a His-tag, or at least one peptidic cleavage site,

A1 is a superfolder green fluorescent protein, which has the amino acid sequence Ser-Lys-Gly-Glu-Glu-Leu-Phe-Thr-Gly-Val-Val-Pro-Ile-Leu-Val-Glu-Leu-Asp-Gly-Asp-Val-Asn-Gly-His-Lys-Phe-Ser-Val-Arg-Gly-Glu-Gly-Glu-Gly-Asp-Ala-Thr-Asn-Gly-Lys-Leu-Thr-Leu-Lys-Phe-Ile-Cys-Thr-Thr-Gly-Lys-Leu-Pro-Val-Pro-Trp-Pro-Thr-Leu-Val-Thr-Thr-Leu-Thr-Tyr-Gly-Val-Gln-Cys-Phe-Ser-Arg-Tyr-Pro-Asp-His-Met-Lys-Arg-His-Asp-Phe-Phe-Lys-Ser-Ala-Met-Pro-Glu-Gly-Tyr-Val-Gln-Glu-Arg-Thr-Ile-Ser-Phe-Lys-Asp-Asp-Gly-Thr-Tyr-Lys-Thr-Arg-Ala-Glu-Val-Lys-Phe-Glu-Gly-Asp-Thr-Leu-Val-Asn-Arg-Ile-Glu-Leu-Lys-Gly-Ile-Asp-Phe-Lys-Glu-Asp-Gly-Asn-Ile-Leu-Gly-His-Lys-Leu-Glu-Tyr-Asn-Phe-Asn-Ser-His-Asn-Val-Tyr-Ile-Thr-Ala-Asp-Lys-Gln-Lys-Asn-Gly-Ile-Lys-Ala-Asn-Phe-Lys-Ile-Arg-His-Asn-Val-Glu-Asp-Gly-Ser-Val-Gln-Leu-Ala-Asp-His-Tyr-Gln-Gln-Asn-Thr-Pro-Ile-Gly-Asp-Gly-Pro-Val-Leu-Leu-Pro-Asp-Asn-His-Tyr-Leu-Ser-Thr-Gln-Ser-Val-Leu-Ser-Lys-Asp-Pro-Asn-Glu-Lys-Arg-Asp-His-Met-Val-Leu-Leu-Glu-Phe-Val-Thr-Ala-Ala-Gly-Ile-Thr-His-Gly-Met-Asp-Glu-Leu-Tyr-Lys (SEQ ID NO:1), or an amino acid sequence that is at least 90%, at least 95%, at least 97%, or at least 99% identical to SEQ ID NO:1, T2 is absent, a His-tag, or at least one peptidic cleavage site, provided that at most one of T1 and T2 is absent, under suitable conditions for expression of the expression vector, thereby producing the fusion protein encoded by the nucleic acid in bacterial inclusion bodies, wherein the suitable conditions comprise an inducer for inducing the host cell to express the expression vector, and wherein the expression level of the target peptide is enhanced as compared to a control where a fusion carrier protein is not used.

2. The method of claim 1, wherein the target peptide is selected from the group consisting of corticorelin, PTH, GLP-1 and its analogs exenatide and liraglutide, enfuvirtide, calcitonin, bivalirudin, ziconotide, sermorelin, somatorelin, secretin, teduglutide, proinsulin, hirudin, growth hormone, growth factors, growth hormone releasing factors, corticotropin, release factor, deslorelin, desmopressin, elcatonin, glucagons, leuprolide, leuteinizing hormone-releasing hormone, somatisation, thyrotropin-releasing hormone, triptorelin, vasoactive intestinal peptide, interferons, parathyroid hormone, BH3 peptides, and a beta-amyloidosis peptide or fragments thereof.

3. The method of claim 1, wherein the peptidic cleavage site is selected from the group consisting of Met, Cys, Pro, Asn, Glu, Tyr, Trp, Lys, Arg, Asn-Gly, Asp-Met-Gln-Asp-Ile (SEQ ID NO:31), Asp-Glu-Val-Asp-Ile (SEQ ID NO:32), Leu-Glu-Val-Asp-Ile (SEQ ID NO:33), Trp-Glu-His-Asp-Ile (SEQ ID NO:34), Leu-Glu-His-Asp-Ile (SEQ ID NO:35), Val-Glu-Ile-Asp-Ile (SEQ ID NO:36), Val-Glu-His-Asp-Ile (SEQ ID NO:37), Ile-Glu-Thr-Asp-Ile (SEQ ID NO:38), Leu-Glu-Thr-Asp-Ile (SEQ ID NO:39), Ile-Glu-Ala-Asp-Ile (SEQ ID NO:40), Asp-Asp-Asp-Asp-Lys (SEQ ID NO:41), Arg-Gly-Glu-Ile (SEQ ID NO:42), Arg-Gly-Asp-Ile (SEQ ID NO:43), Arg-Gly-Asp-Ala (SEQ ID NO:45), Ile-Glu-Pro-Asp-Ile (SEQ ID NO:46), Glu-Asn-Leu-Tyr-Phe-Gln-Gly (SEQ ID NO:3), and Glu-Asn-Leu-Tyr-Phe-Gln-Ser (SEQ ID NO:5).

4. The method of claim 1, wherein the peptidic cleavage site is selected from the group consisting of Met, Lys, Arg, Glu-Asn-Leu-Tyr-Phe-Gln-Gly (SEQ ID NO:3), and Glu-Asn-Leu-Tyr-Phe-Gln-Ser (SEQ ID NO:5).

5. The method of claim 1, wherein the His-tag is composed of three to eight histidine residues.

6. The method of claim 1, wherein the target peptide has a sequence between 10 and 200 amino acids in length.

7. The method of claim 1, wherein the target peptide has a sequence between 20 and about 82 amino acids in length.

8. The method of claim 1, wherein the fusion protein further comprises a peptide cleavage site between the fusion carrier protein and the target peptide.

9. The method of claim 1, wherein the expression vector comprising the nucleic acid is operably linked to a promoter for expression of said nucleic acid sequence coding for the fusion protein.

10. The method of claim 9, wherein the promoter is lac promoter, T7 promoter, Tac promoter, lamda promoter, pL promoter, trc promoter, or pBAD promoter.

* * * * *